US009827439B2

(12) United States Patent
Maxik et al.

(10) Patent No.: US 9,827,439 B2
(45) Date of Patent: Nov. 28, 2017

(54) SYSTEM FOR DYNAMICALLY ADJUSTING CIRCADIAN RHYTHM RESPONSIVE TO SCHEDULED EVENTS AND ASSOCIATED METHODS

(71) Applicant: BIOLOGICAL ILLUMINATION, LLC, Melbourne, FL (US)

(72) Inventors: Fredric S. Maxik, Cocoa Beach, FL (US); David E. Bartine, Cocoa, FL (US); Mark Andrew Oostdyk, Cape Canaveral, FL (US); Matthew Regan, Melbourne, FL (US); Robert R. Soler, Cocoa Beach, FL (US); Gregory Flickinger, Indialantic, FL (US)

(73) Assignee: Biological Illumination, LLC, Melbourne, FL (US)

( * ) Notice: Subject to any disclaimer, the term of this patent is extended or adjusted under 35 U.S.C. 154(b) by 0 days.

(21) Appl. No.: 14/590,557

(22) Filed: Jan. 6, 2015

(65) Prior Publication Data
US 2015/0148871 A1 May 28, 2015

Related U.S. Application Data

(63) Continuation-in-part of application No. 14/494,290, filed on Sep. 23, 2014, now Pat. No. 9,131,573, which
(Continued)

(51) Int. Cl.
*A61N 5/06* (2006.01)
*H05B 33/08* (2006.01)
(Continued)

(52) U.S. Cl.
CPC .......... *A61N 5/0618* (2013.01); *A61M 21/02* (2013.01); *H05B 33/0863* (2013.01);
(Continued)

(58) Field of Classification Search
CPC .......... A61M 21/02; A61M 2021/0027; A61M 2021/0044; A61M 2021/0066;
(Continued)

(56) References Cited

U.S. PATENT DOCUMENTS 1,768,812 A  7/1930 Whiting
5,046,494 A  9/1991 Searfoss et al.
(Continued)

FOREIGN PATENT DOCUMENTS

CN  101 702 421 A  5/2010
EP  0 851 260 A2  7/1998
(Continued)

OTHER PUBLICATIONS

Akashi, Yukio et al., Assessment of Headlamp Glare and Potential Countermeasures: Survey of Advanced Front Lighting System (AFS), U.S. Department of Transportation, National Highway Traffic Safety Administration, Contract No. DTNH22-99-D-07005, (Dec. 2005).
(Continued)

*Primary Examiner* — Gary Jackson
*Assistant Examiner* — Scott T Luan
(74) *Attorney, Agent, or Firm* — Mark Malek; Paul J. Ditmyer; Widerman Malek, PL

(57) ABSTRACT

A method of dynamically adjusting a circadian rhythm comprising the steps of determining a current circadian rhythm status of a circadian rhythm of an observer, accessing a calendar of the observer, and identifying a future event of the observer to precondition for, defined as an identified future event. A preconditioning schedule responsive to the identified future event may then be determined. Furthermore, communication with a light source may be established, and the light source may then be operated to emit light according to the preconditioning schedule.

15 Claims, 9 Drawing Sheets

Related U.S. Application Data is a continuation of application No. 13/968,914, filed on Aug. 16, 2013, now Pat. No. 8,841,864, which is a continuation-in-part of application No. 13/311,300, filed on Dec. 5, 2011, now Pat. No. 8,686,641, application No. 14/590,557, which is a continuation-in-part of application No. 14/573,922, filed on Dec. 17, 2014, now Pat. No. 9,532,423, which is a continuation of application No. 13/803,825, filed on Mar. 14, 2013, now Pat. No. 8,743,023, which is a continuation-in-part of application No. 13/709,942, filed on Dec. 10, 2012, now Pat. No. 8,760,370, and a continuation-in-part of application No. 13/234,371, filed on Sep. 16, 2011, now Pat. No. 8,465,167, and a continuation-in-part of application No. 13/107,928, filed on May 15, 2011, now Pat. No. 8,547,391, said application No. 13/803,825 is a continuation-in-part of application No. 13/652,207, filed on Oct. 15, 2012, now Pat. No. 8,643,276, which is a continuation of application No. 13/174,339, filed on Jun. 30, 2011, now Pat. No. 8,324,808, which is a continuation-in-part of application No. 12/842,887, filed on Jul. 23, 2010, now Pat. No. 8,253,336, application No. 14/590,557, which is a continuation-in-part of application No. 13/775,936, filed on Feb. 25, 2013, and a continuation-in-part of application No. 13/465,781, filed on May 7, 2012.

(60) Provisional application No. 61/948,185, filed on Mar. 5, 2014, provisional application No. 61/923,924, filed on Jan. 6, 2014, provisional application No. 61/643,308, filed on May 6, 2012, provisional application No. 61/643,316, filed on May 6, 2012.

(51) Int. Cl.
| | | |
|---|---|---|
| *A61M 21/02* | (2006.01) | |
| *F21S 9/02* | (2006.01) | |
| *F21V 23/04* | (2006.01) | |
| *A61M 21/00* | (2006.01) | |
| *F21Y 101/00* | (2016.01) | |
| *F21K 9/23* | (2016.01) | |

(52) U.S. Cl.
CPC .......... *A61M 2021/0027* (2013.01); *A61M 2021/0044* (2013.01); *A61M 2021/0066* (2013.01); *A61M 2205/3368* (2013.01); *A61N 2005/0627* (2013.01); *F21K 9/23* (2016.08); *F21S 9/02* (2013.01); *F21V 23/045* (2013.01); *F21Y 2101/00* (2013.01)

(58) Field of Classification Search
CPC ... A61M 2205/3368; A61N 2005/0627; A61N 5/0618; H05B 33/0863; F21S 9/02; F21V 23/045; F21Y 2021/00; F21K 9/23
See application file for complete search history.

(56) References Cited

U.S. PATENT DOCUMENTS

| | | | | |
|---|---|---|---|---|
| 5,163,426 A * | 11/1992 | Czeisler | ................ | A61M 21/00 607/88 |
| 5,167,228 A * | 12/1992 | Czeisler | ................ | A61M 21/00 607/88 |
| 5,176,133 A * | 1/1993 | Czeisler | ................ | A61M 21/00 607/88 |
| 5,221,877 A | 6/1993 | Falk | | |
| 5,304,212 A * | 4/1994 | Czeisler | ................ | A61M 21/00 607/88 |
| 5,523,878 A | 6/1996 | Wallace et al. | | |
| 5,680,230 A | 10/1997 | Kaburagi et al. | | |
| 5,704,701 A | 1/1998 | Kavanagh et al. | | |
| 5,813,753 A | 9/1998 | Vriens et al. | | |
| 5,997,150 A | 12/1999 | Anderson | | |
| 6,027,225 A | 2/2000 | Martin et al. | | |
| 6,140,646 A | 10/2000 | Busta et al. | | |
| 6,259,572 B1 | 7/2001 | Meyer, Jr. | | |
| 6,290,382 B1 | 9/2001 | Bourn et al. | | |
| 6,341,876 B1 | 1/2002 | Moss et al. | | |
| 6,356,700 B1 | 3/2002 | Strobl | | |
| 6,369,517 B2 | 4/2002 | Song et al. | | |
| 6,370,168 B1 | 4/2002 | Spinelli | | |
| 6,459,919 B1 | 10/2002 | Lys et al. | | |
| 6,528,954 B1 | 3/2003 | Lys et al. | | |
| 6,542,671 B1 | 4/2003 | Ma et al. | | |
| 6,561,656 B1 | 5/2003 | Kojima et al. | | |
| 6,577,080 B2 | 6/2003 | Lys et al. | | |
| 6,586,882 B1 | 7/2003 | Harbers | | |
| 6,594,090 B2 | 7/2003 | Kruschwitz et al. | | |
| 6,641,283 B1 | 11/2003 | Bohler | | |
| 6,733,135 B2 | 5/2004 | Dho | | |
| 6,734,639 B2 | 5/2004 | Chang et al. | | |
| 6,762,562 B2 | 7/2004 | Leong | | |
| 6,767,111 B1 | 7/2004 | Lai | | |
| 6,787,999 B2 | 9/2004 | Stimac et al. | | |
| 6,817,735 B2 | 11/2004 | Shimizu et al. | | |
| 6,870,523 B1 | 3/2005 | Ben-David et al. | | |
| 6,871,982 B2 | 3/2005 | Holman et al. | | |
| 6,893,140 B2 | 5/2005 | Storey et al. | | |
| 6,940,101 B2 | 9/2005 | Yano et al. | | |
| 6,945,672 B2 | 9/2005 | Du et al. | | |
| 6,967,761 B2 | 11/2005 | Starkweather et al. | | |
| 6,974,713 B2 | 12/2005 | Patel et al. | | |
| 7,008,559 B2 | 3/2006 | Chen | | |
| 7,009,343 B2 | 3/2006 | Lim et al. | | |
| 7,015,636 B2 | 3/2006 | Bolta | | |
| 7,034,934 B2 | 4/2006 | Manning | | |
| 7,042,623 B1 | 5/2006 | Huibers et al. | | |
| 7,058,197 B1 | 6/2006 | McGuire et al. | | |
| 7,070,281 B2 | 7/2006 | Kato | | |
| 7,072,096 B2 | 7/2006 | Holman et al. | | |
| 7,075,707 B1 | 7/2006 | Rapaport et al. | | |
| 7,083,304 B2 | 8/2006 | Rhoads | | |
| 7,095,053 B2 | 8/2006 | Mazzochette et al. | | |
| 7,144,131 B2 | 12/2006 | Rains | | |
| 7,157,745 B2 | 1/2007 | Blonder et al. | | |
| 7,178,941 B2 | 2/2007 | Roberge et al. | | |
| 7,184,201 B2 | 2/2007 | Duncan | | |
| 7,187,484 B2 | 3/2007 | Mehrl | | |
| 7,213,926 B2 | 5/2007 | May et al. | | |
| 7,234,844 B2 | 6/2007 | Bolta et al. | | |
| 7,246,923 B2 | 7/2007 | Conner | | |
| 7,247,874 B2 | 7/2007 | Bode et al. | | |
| 7,252,408 B2 | 8/2007 | Mazzochette et al. | | |
| 7,255,469 B2 | 8/2007 | Wheatley et al. | | |
| 7,261,453 B2 | 8/2007 | Morejon et al. | | |
| 7,289,090 B2 | 10/2007 | Morgan | | |
| 7,300,177 B2 | 11/2007 | Conner | | |
| 7,303,291 B2 | 12/2007 | Ikeda et al. | | |
| 7,306,352 B2 | 12/2007 | Sokolov et al. | | |
| 7,319,293 B2 | 1/2008 | Maxik | | |
| 7,324,076 B2 | 1/2008 | Lee et al. | | |
| 7,325,956 B2 | 2/2008 | Morejon et al. | | |
| 7,342,658 B2 | 3/2008 | Kowarz et al. | | |
| 7,344,279 B2 | 3/2008 | Mueller et al. | | |
| 7,344,280 B2 | 3/2008 | Panagotacos et al. | | |
| 7,349,095 B2 | 3/2008 | Kurosaki | | |
| 7,353,859 B2 | 4/2008 | Stevanovic et al. | | |
| 7,369,056 B2 | 5/2008 | McCollough et al. | | |
| 7,382,091 B2 | 6/2008 | Chen | | |
| 7,382,632 B2 | 6/2008 | Alo et al. | | |
| 7,384,394 B2 * | 6/2008 | Hursh | ................ | A61B 5/4809 128/920 |
| 7,400,439 B2 | 7/2008 | Holman | | |
| 7,427,146 B2 | 9/2008 | Conner | | |
| 7,429,983 B2 | 9/2008 | Islam | | |
| 7,434,946 B2 | 10/2008 | Huibers | | |
| 7,436,996 B2 | 10/2008 | Ben-Chorin | | |

(56) References Cited

U.S. PATENT DOCUMENTS

| | | |
|---|---|---|
| 7,438,443 B2 | 10/2008 | Tatsuno et al. |
| 7,476,016 B2 | 1/2009 | Kurihara |
| 7,478,322 B2 | 1/2009 | Konttinen |
| 7,479,861 B2 | 1/2009 | Zepke et al. |
| 7,482,636 B2 | 1/2009 | Murayama et al. |
| 7,497,596 B2 | 3/2009 | Ge |
| 7,507,001 B2 | 3/2009 | Kit |
| 7,520,607 B2 | 4/2009 | Casper et al. |
| 7,520,642 B2 | 4/2009 | Holman et al. |
| 7,521,875 B2 | 4/2009 | Maxik |
| 7,528,421 B2 | 5/2009 | Mazzochette |
| 7,530,708 B2 | 5/2009 | Park |
| 7,537,347 B2 | 5/2009 | Dewald |
| 7,540,616 B2 | 6/2009 | Conner |
| 7,556,376 B2 | 7/2009 | Ishak et al. |
| 7,556,406 B2 | 7/2009 | Petroski et al. |
| 7,573,210 B2 | 8/2009 | Ashdown et al. |
| 7,580,130 B2 | 8/2009 | Shannon et al. |
| 7,598,686 B2 | 10/2009 | Lys et al. |
| 7,598,961 B2 | 10/2009 | Higgins |
| 7,605,971 B2 | 10/2009 | Ishii et al. |
| 7,619,372 B2 | 11/2009 | Garrity |
| 7,626,755 B2 | 12/2009 | Furuya et al. |
| 7,633,093 B2 | 12/2009 | Blonder et al. |
| 7,633,779 B2 | 12/2009 | Garrity et al. |
| 7,637,643 B2 | 12/2009 | Maxik |
| 7,670,021 B2 | 3/2010 | Chou |
| 7,677,736 B2 | 3/2010 | Kazasumi et al. |
| 7,678,140 B2 | 3/2010 | Brainard et al. |
| 7,679,281 B2 | 3/2010 | Kim et al. |
| 7,684,007 B2 | 3/2010 | Hull et al. |
| 7,703,943 B2 | 4/2010 | Li et al. |
| 7,705,810 B2 | 4/2010 | Choi et al. |
| 7,708,452 B2 | 5/2010 | Maxik et al. |
| 7,709,811 B2 | 5/2010 | Conner |
| 7,719,766 B2 | 5/2010 | Grasser et al. |
| 7,728,846 B2 | 6/2010 | Higgins et al. |
| 7,732,825 B2 | 6/2010 | Kim et al. |
| 7,748,845 B2 | 7/2010 | Casper et al. |
| 7,748,877 B1 | 7/2010 | Colby |
| 7,759,854 B2 | 7/2010 | Miller et al. |
| 7,766,490 B2 | 8/2010 | Harbers et al. |
| 7,806,575 B2 | 10/2010 | Willwohl et al. |
| 7,819,556 B2 | 10/2010 | Heffington et al. |
| 7,824,075 B2 | 11/2010 | Maxik et al. |
| 7,828,453 B2 | 11/2010 | Tran et al. |
| 7,828,465 B2 | 11/2010 | Roberge et al. |
| 7,832,878 B2 | 11/2010 | Brukilacchio et al. |
| 7,834,867 B2 | 11/2010 | Sprague et al. |
| 7,835,056 B2 | 11/2010 | Doucet et al. |
| 7,841,714 B2 | 11/2010 | Grueber |
| 7,845,823 B2 | 12/2010 | Mueller et al. |
| 7,855,376 B2 | 12/2010 | Cantin et al. |
| 7,871,839 B2 | 1/2011 | Lee |
| 7,880,400 B2 | 2/2011 | Zhoo et al. |
| 7,889,430 B2 | 2/2011 | El-Ghoroury et al. |
| 7,905,637 B2 | 3/2011 | Caluori et al. |
| 7,906,722 B2 | 3/2011 | Fork et al. |
| 7,906,789 B2 | 3/2011 | Jung et al. |
| 7,922,356 B2 | 4/2011 | Maxik et al. |
| 7,928,565 B2 | 4/2011 | Brunschwiler et al. |
| 7,964,883 B2 | 6/2011 | Mazzochette et al. |
| 7,972,030 B2 | 7/2011 | Li |
| 7,976,182 B2 | 7/2011 | Ribarich |
| 7,976,205 B2 | 7/2011 | Grotsch et al. |
| 7,984,989 B2 | 7/2011 | Gruber |
| 8,004,203 B2 | 8/2011 | Maxik |
| 8,016,443 B2 | 9/2011 | Falicoff et al. |
| 8,038,314 B2 | 10/2011 | Ladewig |
| 8,040,070 B2 | 10/2011 | Myers et al. |
| 8,047,660 B2 | 11/2011 | Penn et al. |
| 8,049,763 B2 | 11/2011 | Kwak et al. |
| 8,061,857 B2 | 11/2011 | Liu et al. |
| 8,070,302 B2 | 12/2011 | Hatanaka et al. |
| 8,076,680 B2 | 12/2011 | Lee et al. |
| 8,083,364 B2 | 12/2011 | Allen |
| 8,096,668 B2 | 1/2012 | Abu-Ageel |
| 8,115,419 B2 | 2/2012 | Given et al. |
| 8,149,406 B2 | 4/2012 | Bergman et al. |
| 8,164,844 B2 | 4/2012 | Toda et al. |
| 8,172,436 B2 | 5/2012 | Coleman et al. |
| 8,182,106 B2 | 5/2012 | Shin et al. |
| 8,182,115 B2 | 5/2012 | Takahashi et al. |
| 8,188,687 B2 | 5/2012 | Lee et al. |
| 8,192,047 B2 | 6/2012 | Bailey et al. |
| 8,201,968 B2 | 6/2012 | Maxik et al. |
| 8,207,676 B2 | 6/2012 | Hilgers |
| 8,212,836 B2 | 7/2012 | Matsumoto et al. |
| 8,227,813 B2 | 7/2012 | Ward |
| 8,253,336 B2 | 8/2012 | Maxik et al. |
| 8,256,921 B2 | 9/2012 | Crookham et al. |
| 8,272,763 B1 | 9/2012 | Chinnam et al. |
| 8,274,089 B2 | 9/2012 | Lee |
| 8,297,783 B2 | 10/2012 | Kim |
| 8,297,798 B1 | 10/2012 | Pittman et al. |
| 8,304,978 B2 | 11/2012 | Kim et al. |
| 8,308,318 B2 | 11/2012 | Maxik |
| 8,310,171 B2 | 11/2012 | Reisenauer et al. |
| 8,314,569 B2 | 11/2012 | Adamson et al. |
| 8,319,445 B2 | 11/2012 | McKinney et al. |
| 8,324,808 B2 | 12/2012 | Maxik et al. |
| 8,324,823 B2 | 12/2012 | Choi et al. |
| 8,324,840 B2 | 12/2012 | Shteynberg et al. |
| 8,331,099 B2 | 12/2012 | Geissler et al. |
| 8,337,029 B2 | 12/2012 | Li |
| 8,348,492 B2 | 1/2013 | Mier-Langner et al. |
| 8,378,574 B2 | 2/2013 | Schlangen et al. |
| 8,384,984 B2 | 2/2013 | Maxik et al. |
| 8,401,231 B2 | 3/2013 | Maxik et al. |
| 8,405,299 B2 | 3/2013 | Toda et al. |
| 8,410,717 B2 | 4/2013 | Shteynberg et al. |
| 8,410,725 B2 | 4/2013 | Jacobs et al. |
| 8,427,590 B2 | 4/2013 | Raring et al. |
| 8,441,210 B2 | 5/2013 | Shteynberg et al. |
| 8,446,095 B2 | 5/2013 | Maxik et al. |
| 8,454,197 B2 | 6/2013 | Hauschulte |
| 8,465,167 B2 | 6/2013 | Maxik et al. |
| 8,492,995 B2 | 7/2013 | Maxik et al. |
| 8,525,444 B2 | 9/2013 | Van Duijneveldt |
| 8,531,126 B2 | 9/2013 | Kaihotsu et al. |
| 8,545,034 B2 | 10/2013 | Maxik et al. |
| 8,547,391 B2 | 10/2013 | Maxik et al. |
| 8,643,276 B2 | 2/2014 | Maxik et al. |
| 8,662,672 B2 | 3/2014 | Hikmet et al. |
| 8,672,518 B2 | 3/2014 | Boomgaarden et al. |
| 8,674,613 B2 | 3/2014 | Gray et al. |
| 8,678,787 B2 | 3/2014 | Hirata et al. |
| 8,680,457 B2 | 3/2014 | Maxik et al. |
| 8,686,641 B2 | 4/2014 | Maxik et al. |
| 8,730,558 B2 | 5/2014 | Maxik et al. |
| 8,743,023 B2 | 6/2014 | Maxik et al. |
| 8,754,832 B2 | 6/2014 | Maxik et al. |
| 8,760,370 B2 | 6/2014 | Maxik et al. |
| 8,841,864 B2 | 9/2014 | Maxik et al. |
| 8,866,414 B2 | 10/2014 | Maxik et al. |
| 8,901,850 B2 | 12/2014 | Maxik et al. |
| 9,065,554 B2 | 6/2015 | Wolcott et al. |
| 2002/0113555 A1 | 8/2002 | Lys et al. |
| 2002/0151941 A1 | 10/2002 | Okawa et al. |
| 2004/0052076 A1 | 3/2004 | Mueller et al. |
| 2005/0033119 A1 | 2/2005 | Okawa et al. |
| 2005/0200295 A1 | 9/2005 | Lim et al. |
| 2005/0218780 A1 | 10/2005 | Chen |
| 2005/0267213 A1 | 12/2005 | Gold et al. |
| 2006/0002108 A1 | 1/2006 | Ouderkirk et al. |
| 2006/0002110 A1 | 1/2006 | Dowling et al. |
| 2006/0164005 A1 | 7/2006 | Sun |
| 2006/0215193 A1 | 9/2006 | Shannon et al. |
| 2006/0285193 A1 | 12/2006 | Kimura et al. |
| 2007/0013871 A1 | 1/2007 | Marshall et al. |
| 2007/0041167 A1 | 2/2007 | Nachi |
| 2007/0108846 A1 | 5/2007 | Ashdown |
| 2007/0159492 A1 | 7/2007 | Lo et al. |
| 2007/0165193 A1 | 7/2007 | Kubo et al. |

(56) References Cited

U.S. PATENT DOCUMENTS

| | | |
|---|---|---|
| 2007/0262714 A1 | 11/2007 | Bylsma |
| 2008/0114219 A1* | 5/2008 | Zhang et al. .............. 600/301 |
| 2008/0119912 A1 | 5/2008 | Hayes |
| 2008/0143973 A1 | 6/2008 | Wu |
| 2008/0170398 A1 | 7/2008 | Kim |
| 2008/0198572 A1 | 8/2008 | Medendorp |
| 2008/0225520 A1 | 9/2008 | Garbus |
| 2008/0232084 A1 | 9/2008 | Kon |
| 2008/0232116 A1 | 9/2008 | Kim |
| 2009/0027900 A1 | 1/2009 | Janos et al. |
| 2009/0036952 A1 | 2/2009 | Kao et al. |
| 2009/0059585 A1 | 3/2009 | Chen et al. |
| 2009/0128781 A1 | 5/2009 | Li |
| 2009/0141506 A1 | 6/2009 | Lan et al. |
| 2009/0175041 A1 | 7/2009 | Yuen et al. |
| 2009/0273931 A1 | 11/2009 | Ito et al. |
| 2009/0303694 A1 | 12/2009 | Roth et al. |
| 2010/0001652 A1 | 1/2010 | Damsleth |
| 2010/0006762 A1 | 1/2010 | Yoshida et al. |
| 2010/0051976 A1 | 3/2010 | Rooymans |
| 2010/0053959 A1 | 3/2010 | Ijzerman et al. |
| 2010/0060185 A1 | 3/2010 | Van Duijneveldt |
| 2010/0076250 A1 | 3/2010 | Van Woudenberg et al. |
| 2010/0096993 A1 | 4/2010 | Ashdown et al. |
| 2010/0103389 A1 | 4/2010 | McVea et al. |
| 2010/0121420 A1 | 5/2010 | Fiset et al. |
| 2010/0188022 A1 | 7/2010 | Gerlach et al. |
| 2010/0202129 A1 | 8/2010 | Abu-Ageel |
| 2010/0244700 A1 | 9/2010 | Chong et al. |
| 2010/0244735 A1 | 9/2010 | Buelow |
| 2010/0244740 A1 | 9/2010 | Alpert et al. |
| 2010/0270942 A1 | 10/2010 | Hui et al. |
| 2010/0277084 A1 | 11/2010 | Lee et al. |
| 2010/0315320 A1 | 12/2010 | Yoshida |
| 2010/0321641 A1 | 12/2010 | Van Der Lubbe |
| 2011/0010014 A1* | 1/2011 | Oexman et al. .............. 700/276 |
| 2011/0012137 A1 | 1/2011 | Lin et al. |
| 2011/0037390 A1 | 2/2011 | Ko et al. |
| 2011/0080635 A1 | 4/2011 | Takeuchi |
| 2011/0084614 A1* | 4/2011 | Eisele et al. .............. 315/152 |
| 2011/0115381 A1 | 5/2011 | Carlin |
| 2011/0205738 A1 | 8/2011 | Peifer et al. |
| 2011/0299277 A1 | 12/2011 | Ehara |
| 2011/0310446 A1 | 12/2011 | Komatsu |
| 2012/0002411 A1 | 1/2012 | Ladewig |
| 2012/0019138 A1 | 1/2012 | Maxik et al. |
| 2012/0051041 A1 | 3/2012 | Edmond et al. |
| 2012/0106144 A1 | 5/2012 | Chang |
| 2012/0112640 A1 | 5/2012 | Maxik et al. |
| 2012/0140440 A1 | 6/2012 | Dam et al. |
| 2012/0140461 A1 | 6/2012 | Pickard et al. |
| 2012/0188769 A1 | 7/2012 | Lau |
| 2012/0201034 A1 | 8/2012 | Li |
| 2012/0262902 A1 | 10/2012 | Pickard et al. |
| 2012/0327650 A1 | 12/2012 | Lay et al. |
| 2013/0021792 A1 | 1/2013 | Snell et al. |
| 2013/0021803 A1 | 1/2013 | Pickard et al. |
| 2013/0099696 A1 | 4/2013 | Maxik et al. |
| 2013/0120963 A1 | 5/2013 | Holland et al. |
| 2013/0223055 A1 | 8/2013 | Holland et al. |
| 2013/0278148 A1 | 10/2013 | Maxik et al. |
| 2013/0278172 A1 | 10/2013 | Maxik et al. |
| 2013/0293148 A1 | 11/2013 | Holland et al. |
| 2013/0296976 A1 | 11/2013 | Maxik et al. |
| 2013/0300290 A1 | 11/2013 | Holland et al. |
| 2014/0015438 A1 | 1/2014 | Maxik et al. |
| 2014/0049191 A1 | 2/2014 | Maxik et al. |
| 2014/0049192 A1 | 2/2014 | Maxik et al. |
| 2014/0107735 A1 | 4/2014 | Maxik et al. |
| 2014/0268731 A1 | 9/2014 | Maxik et al. |

FOREIGN PATENT DOCUMENTS

| | | |
|---|---|---|
| EP | 1 671 059 B1 | 4/2007 |
| EP | 1 888 708 A1 | 2/2008 |
| EP | 1 950 491 A1 | 7/2008 |
| EP | 2 094 064 A1 | 8/2009 |
| EP | 2 199 657 A2 | 6/2010 |
| EP | 2 242 335 A1 | 10/2010 |
| EP | 2 292 464 A1 | 3/2011 |
| EP | 2 246 611 A1 | 3/2013 |
| JP | 2005-534155 A | 11/2005 |
| JP | 2007-265804 A | 10/2007 |
| JP | 2008-226567 A | 9/2008 |
| JP | 2010-092993 A | 4/2010 |
| JP | 2011-072388 A | 4/2011 |
| WO | WO 03/098977 A1 | 11/2003 |
| WO | WO 2004/011846 A1 | 2/2004 |
| WO | WO 2006/001221 A1 | 1/2006 |
| WO | 2006039789 A1 | 4/2006 |
| WO | WO 2008/137732 A1 | 11/2008 |
| WO | 2008146219 A1 | 12/2008 |
| WO | 2009-029575 | 3/2009 |
| WO | WO 2009/029575 A1 | 3/2009 |
| WO | WO 2009/121539 A1 | 10/2009 |
| WO | 2010122446 A1 | 10/2010 |
| WO | WO 2012/012245 A2 | 1/2012 |
| WO | WO 2012/064470 A2 | 5/2012 |
| WO | WO 2012/135173 A1 | 10/2012 |
| WO | WO 2012/158665 A2 | 11/2012 |
| WO | WO 2013/085978 A2 | 6/2013 |

OTHER PUBLICATIONS

Arthur P. Fraas, Heat Exchanger Design, 1989, p. 60, John Wiley & Sons, Inc., Canada.

Binnie et al. (1979) "Fluorescent Lighting and Epilepsy" Epilepsia 20(6):725-727.

Boeing, (Jul. 6, 2011), International Space Program, S684-13489 Revision A "ISS Interior Solid State Lighting Assembly (SSLA) Specification", Submitted to National Aeronautics and Space Administration, Johnson Space Center, Contract No. NAS15-10000, pp. 1-60.

Brainard et al., (Aug. 15, 2001), "Action Spectrum for Melatonin Regulation in Humans: Evidence for a Novel Circadian Photoreceptor", The Journal of Neuroscience, 21(16):6405-6412.

Bullough, John et al., "Discomfort Glare from Headlamps: Interactions Among Spectrum, Control of Gaze and Background Light Level", Society of Automotive Engineers, Inc., 2003-01-0296, (2003).

Charamisinau et al. (2005) "Semiconductor laser insert with Uniform Illumination for Use in Photodynamic Therapy" Appl Opt 44(24):5055-5068.

Derlofske et al., "Headlamp Parameters and Glare", Society of Automotive Engineers, Inc., 2004-01-1280, (2004).

European Patent Office's EP International Search Report for Application No. 10174449.8; (Dec. 14, 2010).

ERBA Shedding Light on Photosensitivity, One of Epilepsy's Most Complex Conditions. Photosensitivity and Epilepsy. Epilepsy Foundation. Accessed: Aug. 28, 2009. http://www.epilepsyfoundation.org/aboutepilepsy/seizures/photosensitivity-/gerba.cfm.

Figueiro et al. (2004) "Spectral Sensitivity of the Circadian System" Proc. SPIE 5187:207.

Figueiro et al. (2008) "Retinal Mechanisms Determine the Subadditive Response to Polychromatic Light by the Human Circadian System" Neurosci Lett 438(2):242.

Gabrecht et al. (2007) "Design of a Light Delivery System for the Photodynamic Treatment of the Crohn's Disease" Proc. SPIE 6632:1-9.

H. A El-Shaikh, S. V. Garimella, "Enhancement of Air Jet Impingement Heat Transfer using Pin-Fin Heat Sinks", D IEEE Transactions on Components and Packaging Technology, Jun. 2000, vol. 23, No. 2.

Happawana et al. (2009) "Direct De-Ionized Water-Cooled Semiconductor Laser Package for Photodynamic Therapy of Esophageal Carcinoma: Design and Analysis" J Electron Pack 131(2):1-7.

Harding & Harding (1999) "Televised Material and Photosensitive Epilepsy" Epilepsia 40(Suppl. 4):65.

(56) References Cited

OTHER PUBLICATIONS

Hickcox, Sweater K. et al., Lighting Research Center, "Effect of different colored background lighting on LED discomfort glare perception", Proc. of SPIE, vol. 8484, 84840O-1, (2012).
Jones, Eric D., Light Emitting Diodes (LEDS) for General Lumination, an Optoelectronics Industry Development Association (OIDA) Technology Roadmap, OIDA Report, Mar. 2001, published by OIDA in Washington D.C.
J. Y. San, C. H. Huang, M. H, Shu, "Impingement cooling of a confined circular air jet", In t. J. Heat Mass Transf., 1997. pp. 1355-1364, vol. 40.
Kooi, Frank, "Yellow Lessens Discomfort Glare: Physiological Mechanism(S)", TNO Human Factors, Netherlands, Contract No. FA8655-03-1-3043, (Mar. 9, 2004).
Kuller & Laike (1998) "The Impact of Flicker from Fluorescent Lighting on Well-Being, Perfiormance and Physiological Arousal" Ergonomics 41(4):433-447.
Lakatos (2006) "Recent trends in the epidemiology of Inflammatory Bowel Disease: Up or Down?" World J Gastroenterol 12(38):6102.
Mace, Douglas et al., "Countermeasures for Reducing the Effects of Headlight Glare", The Last Resource, Prepared for the AAA Foundation for Traffic Safety, pp. 1 to 110, (Dec. 2001).
Mehta, Arpit, "Map Colors of a CIE Plot and Color Temperature Using an RGB Color Sensor", Strategic Applications Engineer, Maxim Integrated Products, A1026, p. 1-11, (2005).
N. T. Obot, W. J. Douglas, A S. Mujumdar, "Effect of Semiconfinement on Impingement Heat Transfer", Proc. 7th Int. Heat Transf. Conf., 1982, pp. 1355-1364. vol. 3.
Ortner & Dorta (2006) "Technology Insight: Photodynamic Therapy for Cholangiocarcinoma" Nat Clin Pract Gastroenterol Hepatol 3(8):459-467.
Rea (2010) "Circadian Light" J Circadian Rhythms 8(1):2.
Rea et al. (2010) "The Potential of Outdoor Lighting for Stimulating the Human Circadian System" Alliance for Solid-State Illumination Systems and Technologies (ASSIST), May 13, 2010, p. 1-11.
Rosco Laboratories Poster "Color Filter Technical Data Sheet: #87 Pale Yellow Green" (2001).
S. A Solovitz, L. D. Stevanovic, R. A Beaupre, "Microchannels Take Heatsinks to the Next Level", Power Electronics Technology, Nov. 2006.
Sengupta, Upal, "How to Implement a 5-W Wireless Power System", How2Power Today, pp. 1-8, (Jul. 2010).
Sivak, Michael et al., "Blue Content of LED Headlamps and Discomfort Glare", The University of Michigan Transportation Research Institute, Report No. UMTRI-2005-2, pp. 1-18, (Feb. 2005).
Stevens (1987) "Electronic Power Use and Breast Cancer: A Hypothesis" Am J Epidemiol 125(4):556-561.
Stockman, Andrew, "The spectral sensitivity of the human short-wavelength sensitive cones derived from thresholds and color matches", Pergamon, Vision Research 39, pp. 2901-2927 (1999).
Tannith Cattermole, "Smart Energy Glass controls light on demand", Gizmag.com, Apr. 18, 2010 accessed Nov. 1, 2011.
Topalkara et al. (1998) "Effects of flash frequency and repetition of intermittent photic stimulation on photoparoxysmal responses" Seizure 7(13):249-253.
Veitch & McColl (1995) "Modulation of Fluorescent Light: Flicker Rate and Light Source Effects on Visual Performance and Visual Comfort" Lighting Research and Technology 27:243-256.

Wang (2005) "The Critical Role of Light in Promoting Intestinal Inflammation and Crohn's Disease" J Immunol 174 (12):8173-8182.
Wilkins et al. (1979) "Neurophysical aspects of pattern-sensitive epilepsy" Brain 102:1-25.
Wilkins et al. (1989) "Fluorescent lighting, headaches, and eyestrain" Lighting Res Technol 21(1):11-18.
Yongmann M. Chung, Kai H. Luo, "Unsteady Heat Transfer Analysis of an Impinging Jet", Journal of Heat Transfer—Transactions of the ASME, Dec. 2002, pp. 1039-1048, vol. 124, No. 6.
U.S. Patent and Trademark Office's Non-Final Office Action dated May 23, 2013 cited in related U.S. Appl. No. 13/311,300 (14 pages).
U.S. Patent and Trademark Office's Applicant-Initiated Interview Summary dated Jul. 8, 2013 cited in related U.S. Appl. No. 13/311,300 (5 pages).
U.S. Patent and Trademark Office's Final Office Action dated Aug. 29, 2013 cited in related U.S. Appl. No. 13/311,300 (10 pages).
U.S. Patent and Trademark Office's Applicant-Initiated Interview Summary dated Oct. 30, 2013 cited in related U.S. Appl. No. 13/311,300 (3 pages).
International Searching Authority's PCT International Search Report dated Oct. 21, 2013 cited in related PCT/US2012/067816 (5 pages).
International Searching Authority's PCT Written Opinion dated Oct. 21, 2013 cited in related PCT/US2012/067816 (8 pages).
U.S. Patent and Trademark Office's Non-Final Office Action dated Jul. 14, 2014 cited in related U.S. Appl. No. 13/775,936 (51 pages).
U.S. Patent and Trademark Office's Final Office Action dated Jan. 15, 2015 cited in related U.S. Appl. No. 13/775,936 (60 pages).
U.S. Patent and Trademark Office's Non-Final Office Action dated Jun. 22, 2015 cited in related U.S. Appl. No. 13/775,936 (33 pages).
U.S. Patent and Trademark Office's Non-Final Office Action dated Oct. 1, 2012 cited in related U.S. Appl. No. 13/465,781 (22 pages).
U.S. Patent and Trademark Office's Examiner's Interview Summary Office Action dated Nov. 16, 2012 cited in related U.S. Appl. No. 13/465,781 (4 pages).
U.S. Patent and Trademark Office's Final Office Action dated Feb. 7, 2013 cited in related U.S. Appl. No. 13/465,781 (25 pages).
U.S. Patent and Trademark Office's Final Office Action dated Oct. 11, 2013 cited in related U.S. Appl. No. 13/465,781 (10 pages).
U.S. Patent and Trademark Office's Final Office Action dated Mar. 14, 2014 cited in related U.S. Appl. No. 13/465,781 (9 pages).
U.S. Patent and Trademark Office's $2^{nd}$ or Supplemental Examiner's Answer to Appeal Brief dated Nov. 3, 2014 cited in related U.S. Appl. No. 13/465,781 (18 pages).
U.S. Patent and Trademark Office's Notice of Allowance with Reasons for Allowance dated Mar. 3, 2013 cited in related U.S. Appl. No. 14/315,660 (8 pages).
U.S. Patent and Trademark Office's Office Action dated Apr. 10, 2015 cited in related U.S. Appl. No. 14/494,290 (6 pages).
U.S. Patent and Trademark Office's Notice of Allowance with Reasons for Allowance dated Jun. 24, 2015 cited in related U.S. Appl. No. 14/494,290 (13 pages).
United States Patent Office's Notice of Allowance dated Nov. 9, 2015 cited in related U.S. Appl. No. 13/775,936 (28 pages).
Extended European Search Report dated Nov. 3, 2016 filed in related European Application No. 14774608.5 (7 pages).

\* cited by examiner

SYSTEM FOR DYNAMICALLY ADJUSTING CIRCADIAN RHYTHM RESPONSIVE TO SCHEDULED EVENTS AND ASSOCIATED METHODS

RELATED APPLICATIONS

This application is related to and claims benefit under 35 U.S.C. §119(e) of U.S. Provisional Patent Application Ser. No. 61/948,185 titled System for Dynamically Adjusting Circadian Rhythm Responsive to Schedule Events and Associated Methods filed Mar. 5, 2014 and U.S. Provisional Patent Application Ser. No. 61/923,924 titled Luminaire for Varying Biologically-Adjusted Illumination According to a User-Controllable Circadian Pattern and Associated Systems and Methods filed Jan. 6, 2014, the content of each of which is incorporated herein by reference in their entireties, except to the extent disclosures therein are inconsistent with disclosure herein. Additionally, this application is a continuation-in-part and claims benefit under 35 U.S.C. §120 of U.S. patent application Ser. No. 14/494,290 titled Tunable LED Lamp for Producing Biologically-Adjusted Light filed Sep. 23, 2014, which is in turn a continuation of U.S. patent application Ser. No. 13/968,914 filed Aug. 16, 2013, now U.S. Pat. No. 8,841,864 issued Sep. 23, 2014, titled Tunable LED Lamp for Producing Biologically-Adjusted Light, which is in turn a continuation-in-part of U.S. patent application Ser. No. 13/311,300 filed Dec. 5, 2011, now U.S. Pat. No. 8,686,641 issued Apr. 1, 2014, titled Tunable LED Lamp for Producing Biologically-Adjusted Light. Furthermore, this application is a continuation-in-part of U.S. patent application Ser. No. 14/573,922 titled System and Methods for Operating a Lighting Device filed Dec. 17, 2014, which is, in turn, a continuation of U.S. patent application Ser. No. 13/803,825 filed Mar. 14, 2013 now U.S. Pat. No. 8,743,023 issued Jun. 3, 2014, titled System for Generating Non-Homogenous Biologically-Adjusted Light and Associated Methods filed, which is, in turn, a continuation-in-part of U.S. patent application Ser. No. 13/709,942 filed Dec. 10, 2012, now U.S. Pat. No. 8,760,370 issued Jun. 24, 2014, titled System for Generating Non-Homogenous Light and Associated Methods, which, in turn, claims priority from U.S. Provisional Patent Application Ser. No. 61/643,308 titled Tunable Light System and Associated Methods filed May 6, 2012, U.S. Provisional Patent Application Ser. No. 61/643,316 titled Luminaire Having an Adaptable Light Source and Associated Methods filed May 6, 2012 and is a continuation-in-part of U.S. patent application Ser. No. 13/234,371 filed Sep. 16, 2011, now U.S. Pat. No. 8,465,167 issued Jun. 18, 2013, titled Color Conversion Occlusion and Associated Methods and is also a continuation-in-part of U.S. patent application Ser. No. 13/107,928 filed May 15, 2011, now U.S. Pat. No. 8,547,391 issued Oct. 1, 2013, titled High Efficacy Lighting Signal Converter and Associated Methods, the content of each of which is incorporated by reference herein in their entireties, except to the extent disclosure therein is inconsistent with disclosure herein. Additionally, U.S. patent application Ser. No. 13/803,825 filed Mar. 14, 2013 now U.S. Pat. No. 8,743,023 issued Jun. 3, 2014, titled System for Generating Non-Homogenous Biologically-Adjusted Light and Associated Methods filed is a continuation-in-part of U.S. patent application Ser. No. 13/652,207 filed Oct. 15, 2012, now U.S. Pat. No. 8,643,276 issued Feb. 4, 2014 titled LED Lamp for Producing Biologically-Corrected Light, which, in turn, is a continuation of U.S. patent application Ser. No. 13/174,339 filed Jun. 30, 2011, now U.S. Pat. No. 8,324,808 issued Dec. 4, 2012, titled LED Lamp for Producing Biologically-Corrected Light, which, in turn, is a continuation-in-part of U.S. patent application Ser. No. 12/842,887 filed Jul. 23, 2010, now U.S. Pat. No. 8,253,336 issued Aug. 28, 2012, titled LED Lamp for Producing Biologically-Adjusted Light, the contents of each of which are incorporated by reference in their entireties except to the extent disclosure therein is inconsistent with disclosure herein.

Furthermore, this application is continuation-in-part and claims benefit under 35 U.S.C. §120 of U.S. patent application Ser. No. 13/775,936 filed Feb. 25, 2013 titled Adaptive Light System and Associated Methods and U.S. patent application Ser. No. 13/465,781 filed May 7, 2012 titled Dynamic Wavelength Adapting Device to Affect Physiological Response and Associated Methods, the contents of each of which are incorporated by reference in their entireties except to the extent disclosure therein is inconsistent with disclosure herein.

FIELD OF THE INVENTION

The present invention relates to systems and methods for lighting systems for adjusting circadian rhythms.

BACKGROUND OF THE INVENTION

The issue of discordance between an individual's circadian rhythm and the day-night cycle after traveling across time zones, better known as "jet lag," is well known and documented. This discordance is a result in the rapid change of the day-night cycle timing without adequate time for the individual's circadian rhythm to adjust to the new timing. However, it is increasingly evident that the individual's circadian rhythm can be preconditioned prior to travel so as to mitigate the jet lag of the individual. Additionally, evidence increasingly demonstrates that certain types of activity, e.g. physical activity, mental activity, peak at different periods during the circadian cycle. Accordingly, there is a benefit to syncing one's circadian cycle such that these peak periods coincide with a known event that would benefit from such syncing, e.g. aligning the circadian rhythm to peak physical activity performance at the same time as an athletic event, or syncing peak mental performance to coincide with an academic test. However, such systems as are presently available are imprecise and require significant control by the individual to be useful on a frequent basis. Additionally, such systems require the individual to begin preconditioning with sufficient time in advance of the future event so as to adjust the circadian rhythm of the individual without exceeding a maximum circadian shift in a given day. Accordingly, there is a need for a system that is capable of identifying future events requiring or benefitting from the preconditioning of the individual's circadian rhythm and determining a preconditioning schedule accordingly.

SUMMARY OF THE INVENTION

Accordingly, in light of the above, embodiments of the present invention are directed to systems and methods for the dynamic and automated adjustment of an observer's circadian rhythm. An embodiment of the invention provides a method of dynamically adjusting a circadian rhythm comprising the steps of determining a current circadian rhythm status of a circadian rhythm of an observer, accessing a calendar of the observer, identifying a future event of the observer to precondition for, defined as an identified future event, and determining a preconditioning schedule responsive to the identified future event. The method may further comprise the steps of establishing communication with a light source, and operating the light source to emit light of the preconditioning schedule.

In some embodiments, the method may further comprising the steps of determining the time of day for the observer, determining the time zone of the observer, and determining the date. The step of identifying a future event of the observer to precondition for may comprise the steps of accessing future events within a timeframe from the calendar and determining which future events require preconditioning. Furthermore, upon determination that multiple future events require preconditioning, defined as multiple identified future events, the method may comprise performing the step of determining a preconditioning schedule for each of the multiple identified future events. Additionally, the method may comprise the steps of determining if the any of the preconditioning schedules for the multiple identified future events conflicts, and, upon a determination that no conflict exists, performing the step of operating the light source to emit light of the preconditioning schedules. Upon a determination that a conflict exists, the method may comprise performing the steps of querying a user to select one or more non-conflicting future events, receiving an input from the user indicating one or more future events to precondition for, and operating the light source responsive to the input.

In some embodiments, the step of determining the preconditioning schedule may comprise the steps of identifying the type of circadian shift needed for the future event, determining the magnitude of the circadian shift, determining the timeframe for preconditioning, and determining the magnitude of the per-day shift. Furthermore, the method may further comprise the step of determining if the per-day shift exceeds a maximum allowed per-day shift. Upon a determination that the per-day shift exceeds the maximum allowed per-day shift, the method may comprise performing the steps of querying the user as to whether to override the maximum allowed per-day shift, receiving an input from the user responsive to the query of whether to exceed the maximum per-day shift, and selecting a preconditioning schedule responsive to the user input. The maximum allowed per-day shift is 2.5 hours.

In some embodiments, the method of may further comprise the steps of monitoring a sleep cycle of the observer and implementing changes to the preconditioning schedule responsive to the sleep cycle of the observer. The step of monitoring a sleep pattern of the observer may comprise the steps of determining if the observer is asleep, recording signals from a sensor, identifying and recording an indication of low quality sleep from the signals received from the sensor, and determining changes to the preconditioning schedule responsive to the indication of the low quality sleep. The sensor may be at least one of an optical motion detector and an acceleration detector. Additionally, the method may further comprise the steps of iteratively observing if the observer is asleep, recording indications of low quality sleep, and waiting for the next indication of low quality sleep until the observer is awake. Furthermore, responsive to an indication of low quality sleep, the method may comprise performing the steps of determining whether an environmental condition of a sleeping environment associated with the observer is outside a target range, defined as an environmental change recommendation, and signaling an environmental control system responsive to the environmental change recommendation. The environmental control system may be an HVAC system.

An additional embodiment of the present invention is directed to a lighting system for dynamically adjusting a circadian rhythm of an observer, the lighting system comprising a lighting device. The lighting device may comprise a housing a control circuitry, a memory, and a light source positioned in communication with and controlled by the control circuitry. The memory may comprise a calendar associated with the user comprising a future event. Furthermore, the control circuitry may be configured to identify a future event from the calendar to precondition a circadian rhythm of the observer, defined as the identified future event. Additionally, the control circuitry may be configured to determine a preconditioning schedule for the identified future event, and to operate the light source according to the preconditioning schedule.

In some embodiments, the lighting device may further comprise a communication device positioned in communication with the control circuitry and configured to communicate across a network. The communication device may be configured to access a calendar and identify future events associated with the observer across the network.

BRIEF DESCRIPTION OF THE DRAWINGS

FIG. 4b is a side sectional view taken through line b-b of the system of FIG. 1a.

DETAILED DESCRIPTION OF THE INVENTION

Figure 1:
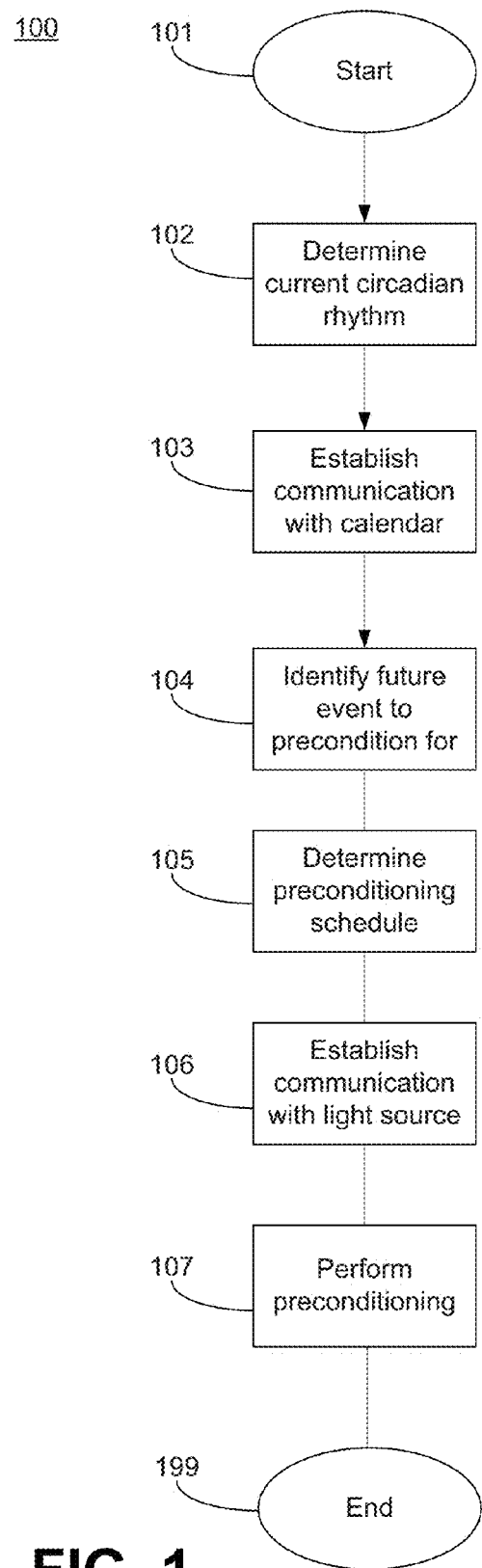
FIG. 1 is a method of operating a lighting device responsive to a calendared event according to an embodiment of the invention.

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Those of ordinary skill in the art realize that the following descriptions of the embodiments of the present invention are illustrative and are not intended to be limiting in any way. Other embodiments of the present invention will readily suggest themselves to such skilled persons having the benefit of this disclosure. Like numbers refer to like elements throughout.

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the claimed invention.

In this detailed description of the present invention, a person skilled in the art should note that directional terms, such as "above," "below," "upper," "lower," and other like terms are used for the convenience of the reader in reference to the drawings. Also, a person skilled in the art should notice this description may contain other terminology to convey position, orientation, and direction without departing from the principles of the present invention.

Furthermore, in this detailed description, a person skilled in the art should note that quantitative qualifying terms such as "generally," "substantially," "mostly," and other terms are used, in general, to mean that the referred to object, characteristic, or quality constitutes a majority of the subject of the reference. The meaning of any of these terms is dependent upon the context within which it is used, and the meaning may be expressly modified.

An embodiment of the invention text, as shown and described by the various figures and accompanying text, provides a system for causing illumination that is viewable by an observer to shift a circadian rhythm of the observer responsive to a calendared event for the observer. The means by which the illumination is caused to affect the shift may vary, including adjustment of the spectral power distribution (SPD) of light emitted by a light source associated with a user device, adjustment of the SPD of a lighting device in communication with a user device, or filtering of light emitted by a light source prior to observation by the observer by a filtering device. In each case, the determination of whether and how to cause a circadian shift in the observer may be made based upon the identification of an upcoming event on a calendar associated with the observer, evaluation of the SPD of light currently visible by the observer, and adjustment thereof.

Referring now to FIG. 1, a flowchart illustrating a method 100 of operating a lighting device responsive to a calendared event is presented. Starting at Block 101, the system may determine the current circadian rhythm of an observer of a lighting device at Block 102. The determination of the current circadian rhythm may include at least determining an approximate waking time and an approximate sleeping time of the observer. More specifically, the determination of the current circadian rhythm may include at least determining at what time the observer wakes up and what time the observer goes to sleep. More information regarding the determination of the current circadian rhythm of the observer may be found in U.S. Provisional Patent Application Ser. No. 61/936,654 titled System for Detecting and Analyzing Motion for Pattern Prediction and Associated Methods filed Feb. 6, 2014 and U.S. Provisional Patent Application Ser. No. 61/785,209 titled Method for Controlling Blood Glucose Production filed Mar. 14, 2013, the contents of each of which are incorporated by reference in their entirety, except to the extent disclosures made therein are inconsistent with disclosures made herein. In some embodiments, the system may infer an approximate wake-up time and going to sleep time based on the calendar of the observer, which will be discussed in greater detail hereinbelow. Accordingly, although the step of determining the current circadian rhythm is disclosed first in the method 100, it is not necessarily performed first in time in every embodiment of the invention.

Next, at Block 103, the system may establish communication with the calendar associated with the observer. Establishing communication with the calendar may be accomplished by various means a method, as will be discussed in greater detail hereinbelow. The calendar may include a variety of events.

Upon establishing communication with the calendar, at Block 104 the system may identify a future event on the calendar associated with the observer to precondition for. The term "precondition" may be understood to include the meaning of shifting the circadian rhythm of the observer so as to align the observer's circadian rhythm with the future event. More information regarding affecting a circadian shift may be found in U.S. patent application Ser. No. 13/968,875 titled Tunable LED Lamp for Producing Biologically-Adjusted Light filed Aug. 16, 2013, the content of which is incorporated by reference in its entirety herein, except to the extent disclosure made therein is inconsistent with disclosure made herein, and U.S. Provisional Patent Application Ser. No. 61/785,209, which is incorporated by reference hereinabove.

At Block 105, the system may determine a preconditioning schedule. The preconditioning schedule may be configured to shift the circadian rhythm of the observer incrementally between the present time and time associated with the future event. More specifically, the system may determine a day-by-day schedule of lighting configurations that are configured to shift the circadian rhythm of the observer. More information regarding a daily lighting schedule, and the identification of patterns associated therewith, may be found in U.S. Provisional Patent Application Ser. No. 61/923,924 titled Luminaire for Varying Biologically-Adjusted Illumination According to a User-Controllable Circadian Pattern and Associated Systems and Methods filed Jan. 6, 2014, the content of which is incorporated by reference in its entirety herein, except to the extent disclosure made therein is inconsistent with disclosure made herein.

At Block 106, the system may establish communication with a light source. The type of communication the system establishes with the light source may depend on the nature of the system. In some embodiments, the system may be configured to directly control the operation of the light source, in which case the electrical communication with the light source will likely have already been established. Some embodiments, the system may be configured to establish technical communication with the light source across a network, as will be described in greater detail hereinbelow. In such embodiments, the system may so establish electrical communication with the light source, either directly or indirectly through an intermediate computerized device, such as a microcontroller. In some embodiments, the system may be configured to be positioned in optical communication with the light source. In such embodiments, the element of the system may be positioned intermediate the light source and the observer, such that all light emitted by the light source must first pass through the element of the system prior to being observed by the observer.

At Block 107, the system may begin performing preconditioning according to the preconditioning schedule determined at Block 105. Depending upon the requirements of the preconditioning schedule, the system may begin increasing or reducing the intensity of light within certain wavelength ranges so as to affect a biological response in the observer. In some embodiments, this may be accomplished by the system controlling the operation of the light source so as to alter the SPD of light emitted thereby. In some embodiments, this may be accomplished by applying an optical filter to the light source so as to reduce the activity of light within one or more wavelength ranges. More information regarding the various embodiments that the system may take is provided hereinbelow. The system may end at Block 199.

Additionally, in some embodiments, the step of performing the preconditioning may include communication with the observer regarding certain activities he or she may engage in or abstain from so as to enhance the effectiveness of the preconditioning. For example, the preconditioning may include recommended times at which to wake up, go to sleep, eat meals, exercise, and the like. Moreover, the preconditioning may include suggesting the observer consume or avoid certain foods and drinks, such as avoiding caffeine or other substances that may affect sleep quality. In some embodiments, the communication to the observer may take the form of entering new events onto the calendar associated with the observer, sending a message to the observer by any method known in the art, including text message, e-mail, and the like, to any phone number or e-mail address associated with the observer. Additionally, in some embodiments, an application for a smartphone, as is known in the art, may provide the above-described communications on a smartphone of the observer.

Figure 2:
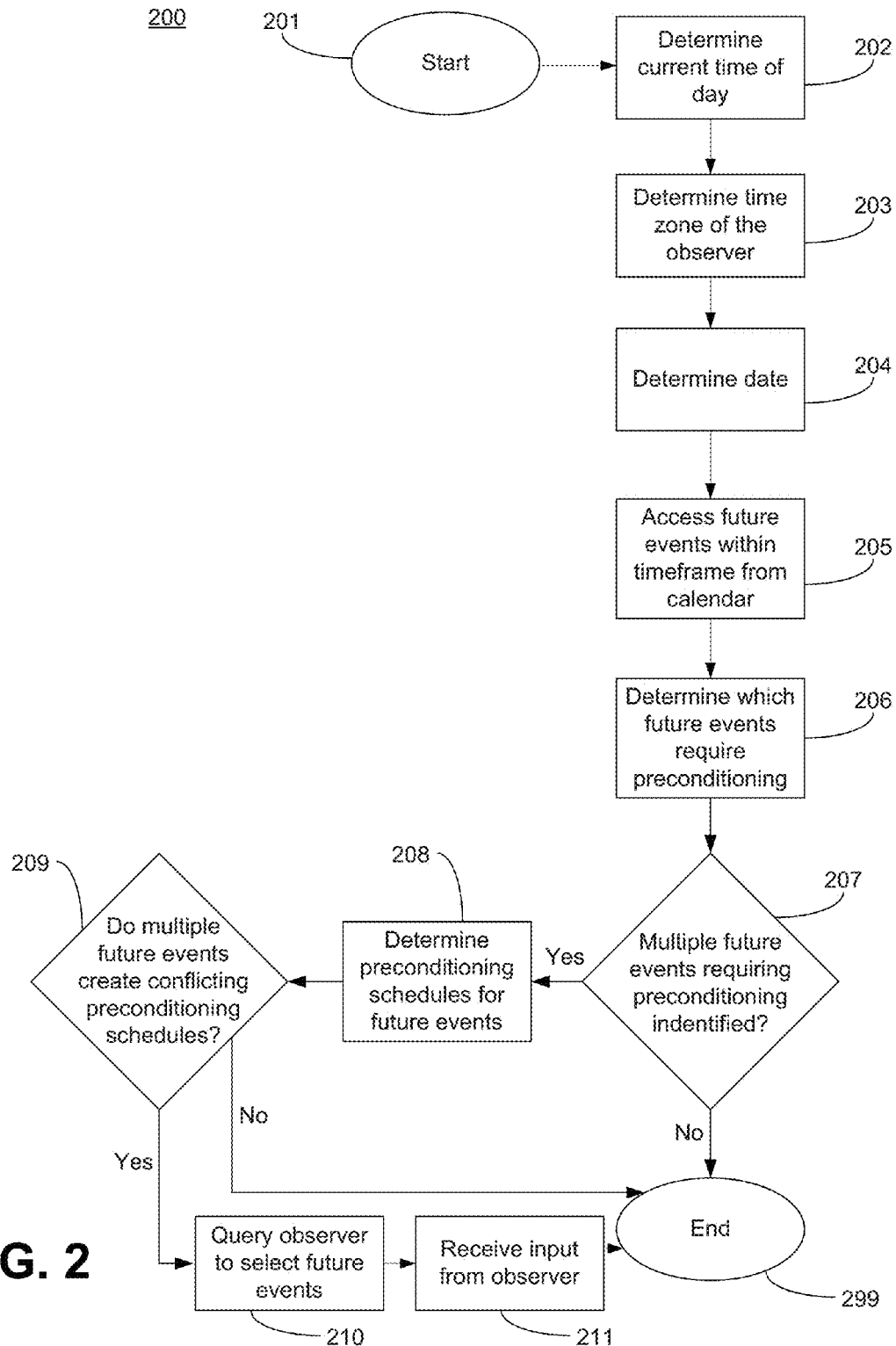
FIG. 2 is a method of identifying a future event requiring preconditioning according to the embodiment depicted in FIG. 1.

Referring now to FIG. 2, additional details regarding the determination of a future event to precondition for are discussed. More specifically, the step of identifying the future event may comprise the steps illustrated in method 200 depicted in FIG. 2. Starting at Block 201, the system may first determine a current time of day at Block 202. In such embodiments, the system may include a clock that is configured to provide a time of day. Additionally, in some embodiments, the system may be configured to receive an indication of the time of day from an outside source across a network, such as the Internet, as is known in the art. Furthermore, in some embodiments, where the system includes a smartphone or other similar device, including a calendar feature, the time of day may be determined by accessing the time of day as maintained by the calendar feature of the smartphone.

Continuing at Block 203, the system may determine a current time zone of the observer. In some embodiments, the system may be configured to determine time zone by receiving an indication from a location lighting device associated with the system. Types of devices include, but are not limited to, a global positioning system (GPS) device. Additionally, in some embodiments, the system may be configured to determine the time from by analyzing an IP address assigned to a network interface device associated with the system, as is known in the art. In each case, the geographical location indicated thereby may be compared to a map delineating the various time zones. In some embodiments, the map may be stored locally on the system. In some embodiments, the map may be accessible by the system via the Internet. Any method of determining the times of associated with the current position of the system is contemplated included within the scope of the invention. Additionally, it is contemplated and included within the scope of the invention that information regarding the time zone of the observer may be determined concurrently with the determination of the time of day, and as such may not constitute a discrete step.

At Block 204, a date associated with the time of day and the time zone associated with the observer may be determined. The date may be determined according to any of the methods described hereinabove related to the determinations of the time of day and the time zone.

At Block 205, the system may access all future events for a given time frame from the calendar. The timeframe for which future events are accessed may be configured by the user, who, in some embodiments, may be the observer. A default configuration may be all future events occurring within the range from about one day in the future to about 12 days in the future. Any timeframe may be selected, and any range from one day to 365 days is contemplated included within the scope of the invention.

At Block 206, the system may analyze the accessed future events to determine which, if any, required or would benefit from preconditioning. The analysis performed by the system may include various considerations. As the nature of the event, the time of day in which the event is to occur, and the time zone in which the event is to occur. For example, the system may identify that an event requiring physical activity may be scheduled to occur at a time that does not coincide with the optimal window of time in the observer's circadian rhythm for physical activity. As another example, the system may identify an event requiring mental performance that may not coincide with the optimal window of time in the observer's circadian rhythm for mental activity. As another example, the system may identify an event scheduled to occur in a time zone that is different than the present time zone of the observer. The scenarios provided herein are exemplary only, and any situation whereby a shift in the circadian rhythm of the observer that may advantageously align the observer's circadian rhythm so as to best correspond to the future event is contemplated included within the scope of the invention.

Additionally, in order for the system to be able to perform the analysis, it is contemplated and included within the scope of the invention that the future events contained in the calendar include information sufficient to be analyzed by the system in order to make the above determinations regarding the nature of the event, the time of day the event is to take place, in the time zone in which event is to occur. As to the nature of the event, a brief description of the event may be included, such as, for example, indicating the observer is to play in a sporting event, indicating the observer is to take an academic test, or any other scenario that may suggest a need for physical and/or mental performance. As to the time of day of the event, an indication of the time may be included. As to the time zone of the event, and address, or at least an identification of the city, state, and/or country within which the event is to occur may be included. Moreover, the system may include software capable of interpreting the information included with each event so as to perform the above analysis.

In the event it is determined that no future events require precondition, the system may cease performance of method 200 as well as method 100 of FIG. 1.

At Block 207, the system may determine if more than one future event requiring preconditioning has been identified. If it is determined at Block 207 that there is not more than one future event requiring preconditioning, the method 200 may end at Block 299. However, if it is determined at Block 207 that multiple future events require preconditioning, the system may determine a preconditioning schedule for each future event at Block 208. Then, at Block 209, the system may compare the preconditioning schedules of each of the future events to determine if the preconditioning schedules for the future events would create a conflict between their respective preconditioning schedules, whereby the system could not concurrently precondition the observer for both future events. If the preconditioning for the future events does not create a conflict, the method 200 may end at Block 299. However, if the preconditioning for the future events does create a conflict, the system may query the user to select one or more future events to precondition for that does not create a conflict at Block 210. Accordingly, the system may either comprise, or be positioned in electrical communication with, a user interface including a user input device. The system may receive an input from the user at Block 211 indicating which of the future events to precondition for. The method may then end at Block 299.

Figure 3:
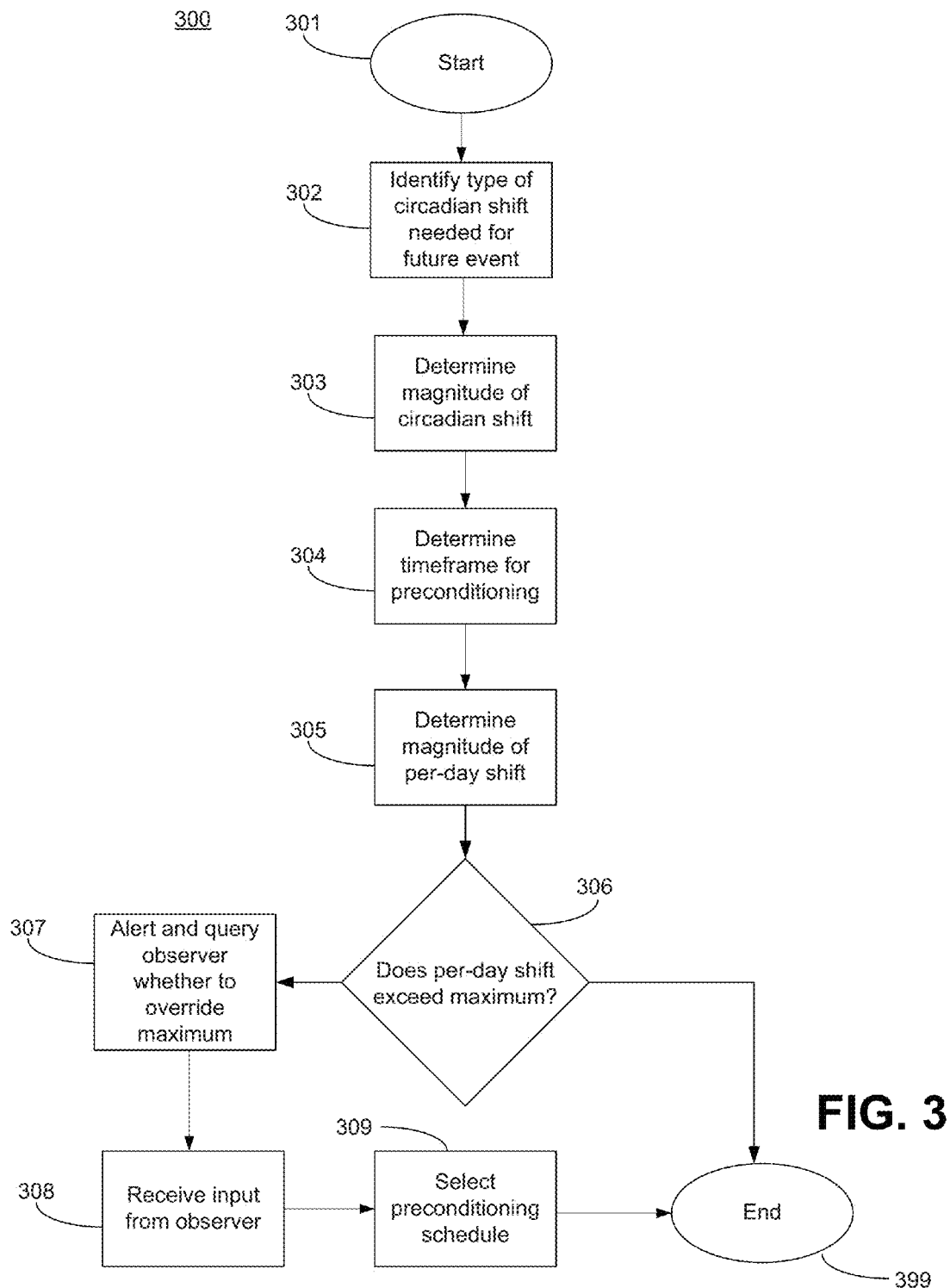
FIG. 3 is a method of determining a preconditioning schedule according to the embodiment depicted in FIG. 1.

Referring now to FIG. 3, additional aspects of the system will now be discussed. Specifically, FIG. 3 illustrates a method 300 related to the determination of the preconditioning schedule will now be discussed. More specifically, the step of determining the preconditioning schedule may comprise the steps illustrated in method 300 depicted in FIG. 3. Beginning at Block 301, the system may analyze the future event to precondition for to identify what type of circadian shift at Block 302, i.e. whether the circadian rhythm of the observer must be advanced or delayed. More information regarding circadian shifts may be found in U.S. Provisional Patent Application Ser. No. 61/785,209, which is incorporated by reference hereinabove.

At Block 303, the system may determine the magnitude of the circadian shift needed to precondition for the future event. The magnitude may be understood to me the time difference between the current state of the observer's circadian rhythm and the future state upon performance of the preconditioning.

At Block 304, the system may determine the timeframe within which the preconditioning is to be accomplished. This may be understood to mean the difference between the present time and date and the time and date of the future event.

At Block 305, the system may calculate the magnitude by which the circadian rhythm must be shifted per-day to precondition in time for the event, i.e. how many hours/minutes must the circadian rhythm be advanced/delayed per-day.

At Block 306, the system may determine if the magnitude of the shift per-day exceeds a maximum per-day magnitude. In the present embodiment, the default maximum per-day magnitude is about two and a half (2.5) hours. The maximum per-day magnitude may be adjusted by a user, and any maximum per-day magnitude, greater or less than two hours, is contemplated and included within a scope of the invention. If it is determined at Block 306 that the per-day magnitude does not exceed the maximum, the method 300 may end at Block 399.

If it is determined at Block 306 that the per-day magnitude does exceed the maximum, an alert may be presented to the observer advising of such at Block 307 and the system may query the user whether to create a preconditioning schedule that exceeds the maximum or that adheres to the maximum and will not be designed to fully precondition the observer. The system may receive an input from the observer at Block 308 selecting either a preconditioning schedule either exceeding or adhering to the maximum. At Block 309 the system may then select the preconditioning schedule that either exceeds or adheres to the maximum responsive to the input received from the observer at Block 308. The method 300 may then end at Block 399.

Figure 4A:
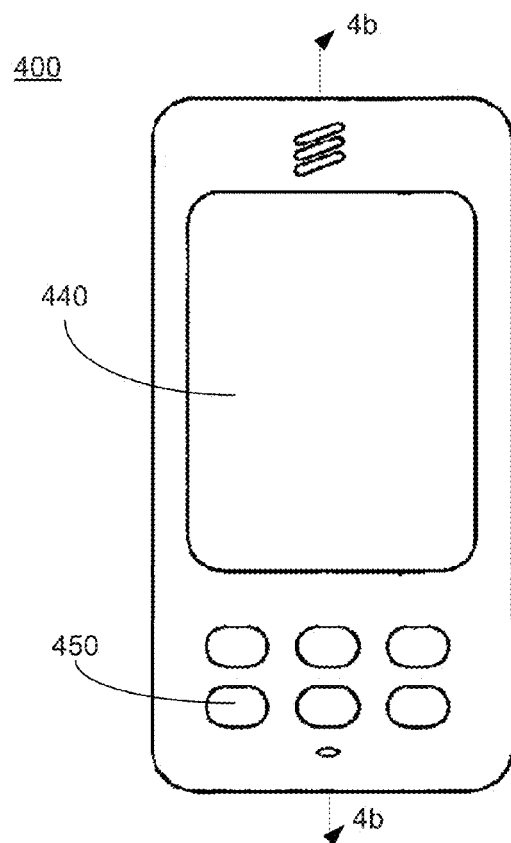
FIG. 4a is an environmental view of a system according to an embodiment of the invention.
Figure 4B:
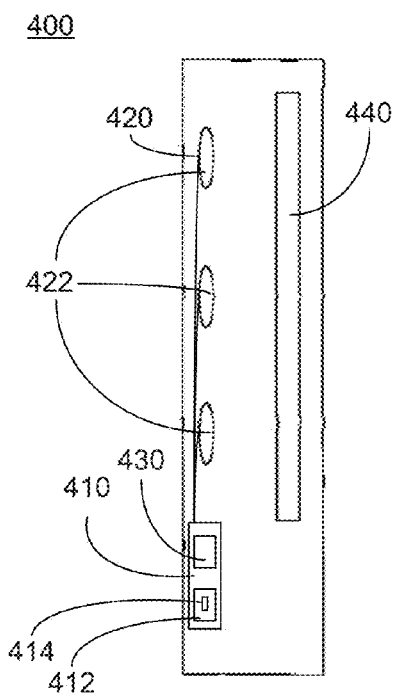

Referring now to FIGS. 4a-b, a system according to an embodiment of the invention is presented. The embodiment may include a user device 400. The user device 400 may be any device capable of emitting light that is observable by an observer. Moreover, the user device 400 may be any device that is capable of adjusting the SPD of light emitted thereby so as to affect a biological response in the observer. More information regarding affecting a biological response in an observer may be found in U.S. patent application Ser. No. 13/968,875 and U.S. Provisional Patent Application Ser. No. 61/923,924, both of which are incorporated by reference hereinabove. Additionally, in the present embodiment, the user device 400 may be any device that is capable of accessing a calendar associated with the observer, identifying an event to adjust light emitted thereby response to, and determining a preconditioning schedule to emit light to affect a shift in the circadian rhythm of the observer. Accordingly, as in the present embodiment, the user device 400 may include control circuitry 410. The control circuitry 410 may have associated therewith a memory 412. In some embodiments, the memory 412 may have stored thereon a calendar 414 associated with an observer.

With reference to the methods of operation illustrated in FIGS. 1-3, the control circuitry 410 may be configured to perform the operations illustrated therein and disclosed in the accompanying description. The various analyses, determinations, and identifications performed by the system described hereinabove may be performed by the control circuitry 410. Additionally, the control circuitry 410 may establish communication with a light source 420 electrically and control operation thereof, as will be described in greater detail hereinbelow.

Additionally, the user device 400 may include a light source 420. The light source 420 may be any type of lighting device as is known in the art, including, but not limited to, light-emitting semiconductors, such as light-emitting diodes (LEDs), incandescent lighting devices, halogen lighting devices, florescent lighting devices, and the like. In the present embodiment, the light source 420 may comprise a plurality of LEDs. In the present embodiments, the light source 420 comprises a plurality of LED banks 422, each LED bank 422 comprising a plurality of LED dies. More information regarding the LEDs and light emitted thereby may be found in U.S. patent application Ser. No. 13/311,300 titled Tunable LED Lamp for Producing Biologically-Adjusted Light filed Dec. 5, 2011, the content of which is incorporated by reference herein except to the extent disclosure therein is inconsistent with disclosure herein.

Additionally, the light source 420 may be operable to emit light so as to affect a biological change in an observer. Specifically, the light source 420 may be operable to affect a circadian shift in an observer, as described hereinabove. Furthermore, the light source 420 may be operable to emit light so as to avoid affecting a biological change in an observer. For example, the light source 420 may be operable so as to suppress the secretion of a hormone, such as, for example, melatonin. Melatonin is an exemplary hormone only, and any hormone that may have its secretion suppressed by the observation of light by an observer is contemplated and included within the scope of the invention. More information regarding the suppression of the secretion of hormones may be found in U.S. patent application Ser. No. 13/311,300 and U.S. Provisional Patent Application Ser. No. 61/785,209, both of which are incorporated by reference hereinabove. Furthermore, any other physiological effect that may result in the shifting of the circadian rhythm and may be affected by the observation of light by an observer is contemplated and included within the scope of the invention.

Accordingly, because the control circuitry 410 is positioned in electrical communication with and is configured to control the operation of the light source 420, the control circuitry may be configured to operate the light source 420 according to a preconditioning schedule. More specifically, the control circuitry 410 may be configured to control the SPD of light emitted by the light source 420 so as to shift a circadian rhythm of the observer so as to align the observer's circadian rhythm with a future event.

Additionally, in some embodiments, the user device 400 may include a network communication device 430. The network communication device 430 may be configured to position the user device 400 in communication with a network. Types of networks include, but are not limited to, wireless communication networks, including cellular data networks, Wi-Fi networks, Bluetooth communication, Zigbee communication, and the Internet. The control circuitry 410 may be positioned in communication with a remotely stored calendar associated with the observer via the network communication device 430. In some embodiments, the control circuitry 410 may be configured to store locally a copy of the remotely stored calendar that is accessible via the network communication device 430, the locally stored calendar being the calendar 414 stored on the memory 412. Moreover, the control circuitry 410 may be configured to update the calendar 414 by accessing the remotely stored calendar, identifying differences between the remotely stored calendar and the calendar 414 stored on the memory 412, and updating the calendar 414 responsive to the identified differences.

The present embodiment, the user device 400 may be a computerized device having a display 440. The display 440 may be any device capable of displaying visual content as is known in the art. Types of displays include, but are not limited to, liquid-crystal displays (LCD), cathode ray tube displays (CRT), digital light processing displays (DLP), plasma displays, and the like. The types of displays listed herein are exemplary only, and all displays other known in the art are contemplated included within the scope of the invention. In the present embodiment, the display 440 may be an LCD that is backlit by the light source 420. More specifically, the light source 420 may emit light that passes through the display 440, the SPD of light emitted by the light source 420 being altered thereby prior to observation by the observer.

In some embodiments, the display 440 may be a touch display, capable of receiving inputs from the user via the user touching the screen, either with a finger or a stylus. In such embodiments, user inputs described in FIGS. 1-3 may be received via the display 440. In some embodiments, the user device 400 may include a keypad 450. They keypad 450 may be configured to receive input from the user by the user pressing a key of the keypad 450. These means and methods of user input are exemplary only, and any means or method of receiving an input from the user are contemplated and included within the scope of the invention.

Figure 5A:
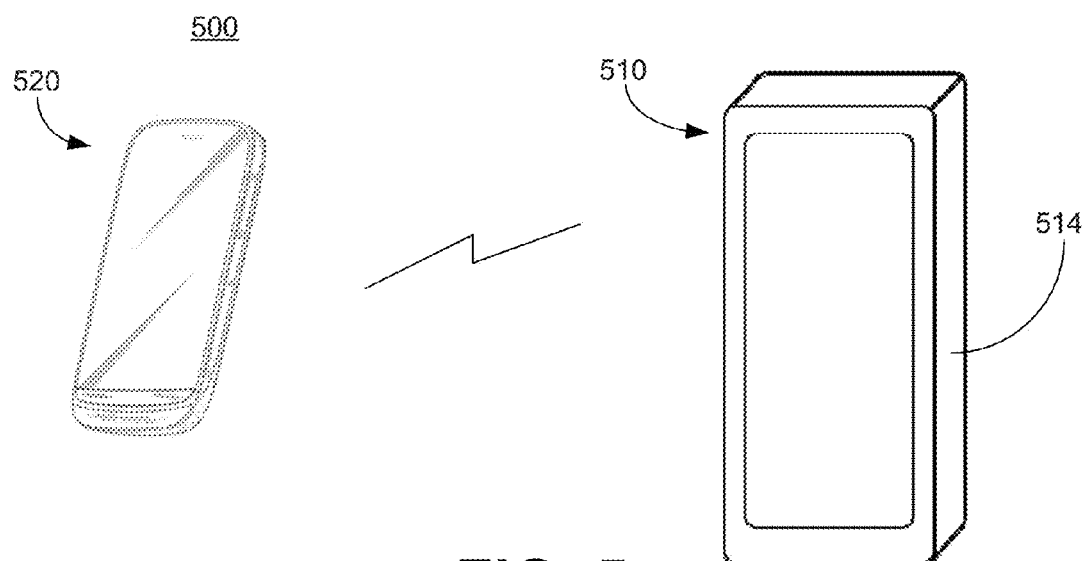
FIG. 5a is an environmental view of a lighting system according to an embodiment of the invention.
Figure 5B:
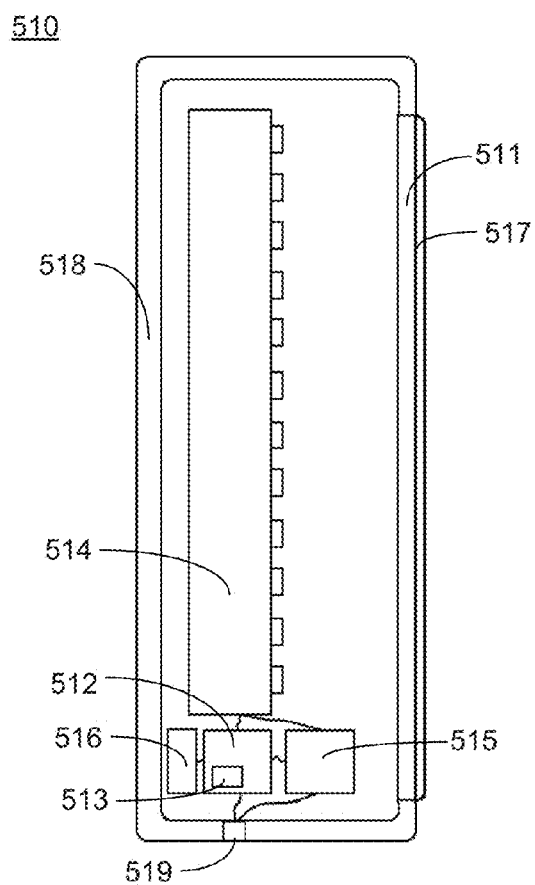
FIG. 5b is a side sectional view of a lighting device of the lighting system of 5a taken through line 5b-5b.

Referring now to FIGS. 5a-b, an embodiment of the invention is presented. In the present embodiment, a lighting system 500 is provided. The lighting system 500 may include a lighting device 510. The lighting device 510 may be configured to emit light in varying configurations as described in references incorporated hereinabove. Accordingly, the lighting device 510 may include control circuitry 512, a light source 514, and a communication device 516. The control circuitry 512 may be positioned in electrical communication with the light source 514 so as to control the operation thereof to emit light having a varying SPD. Additionally, the control circuitry 512 may be positioned in electrical communication with the communication device 516 and be configured to receive signals thereby and to operate the light source 514 responsive to signals received therefrom. Furthermore, the control circuitry 512 may include a memory 513 as described hereinabove. The lighting device 510 may further comprises a housing 518 configured to generally enclose each of the control circuitry 512, the light source 514, and the communication device 516. The housing 518 may include an electric port 519 configured to be positioned in electrical communication with an external supply of electrical power. The control circuitry 512 may be positioned in electrical communication with the electric port 519 and may further be configured to condition electrical power received from the electric port 519 for use by the various electrical components of the lighting device 510, including the light source 514 and the communication device 516.

Additionally, in some embodiments, the lighting device 510 may include a power storage device 515. The power storage device 515 may be positioned in electrical communication with at least each of the control circuitry 512, the light source 514, and the electric port 519, and in some embodiments the communication device 516. The power storage device 515 may be configured to store electric power therein when the electric port 519 is receiving electrical power from an external power source. Additionally, the power storage device 515 may be configured to provide electrical power to elements of the lighting device 510 electrically connected thereto when the electric port 519 is not presently receiving electrical power from an external power source. The power storage device 515 may be any device known in the art capable of storing electrical power, including, but not limited to, batteries and capacitors, including super capacitors and ultra capacitors.

The lighting device 510 may be configured to emit light that is viewable by an observer. More specifically, the light source 514 may be configured to emit light so as to be emitted by the lighting device 510 into the environment surrounding the lighting device 510 so as to be viewable by an observer. In some embodiments, the lighting device may have an emitting aperture 511 through which light emitted by the light source may propagate and be emitted into the environment surrounding the lighting device 510. In some embodiments, the emitting aperture 511 may have positioned therein an optic 517. The optic 517 may be carried by the housing 518. Furthermore, the optic 517 may be transparent or translucent. The optic 517 may be configured to affect the direction light propagating therethrough is emitted therefrom through at least one of reflection or refraction.

The lighting system 500 may further include a user device 520. The user device 520 may be an electrical device configured to electronically communicate with the lighting device 510 so as to provide instructions thereto regarding operation thereof. Accordingly, the user device 520 may be configured to communicate with the communication device 516 of the lighting device 510 by any means or method known in the art, including those methods and standards of communication described hereinabove.

Additionally, the user device 520 may be configured to provide information to a user, who may be the observer, visually, as well as receive inputs therefrom related to the operation of the lighting device 510. The user device 520 may further be configured to receive inputs from the user, and to transmit those inputs to the lighting device 510. The user device 520 may include any type of user input known in the art, including, but not limited to, keypads, keyboards, a mouse, touchscreen displays, and voice recognition. Any other method of receiving an input from the user is contemplated and included within the scope of the invention.

While the form of the lighting device 510 of the present embodiment is that of a standalone lighting fixture, is it contemplated and included within the scope of the invention that the lighting device 510 may take the form of any lighting device, including, but not limited to, lamps, bulbs, luminaires, and the like. Therefore, any light-emitting device that may perform the above-described functions is contemplated and included within the scope of the invention.

Figure 6:
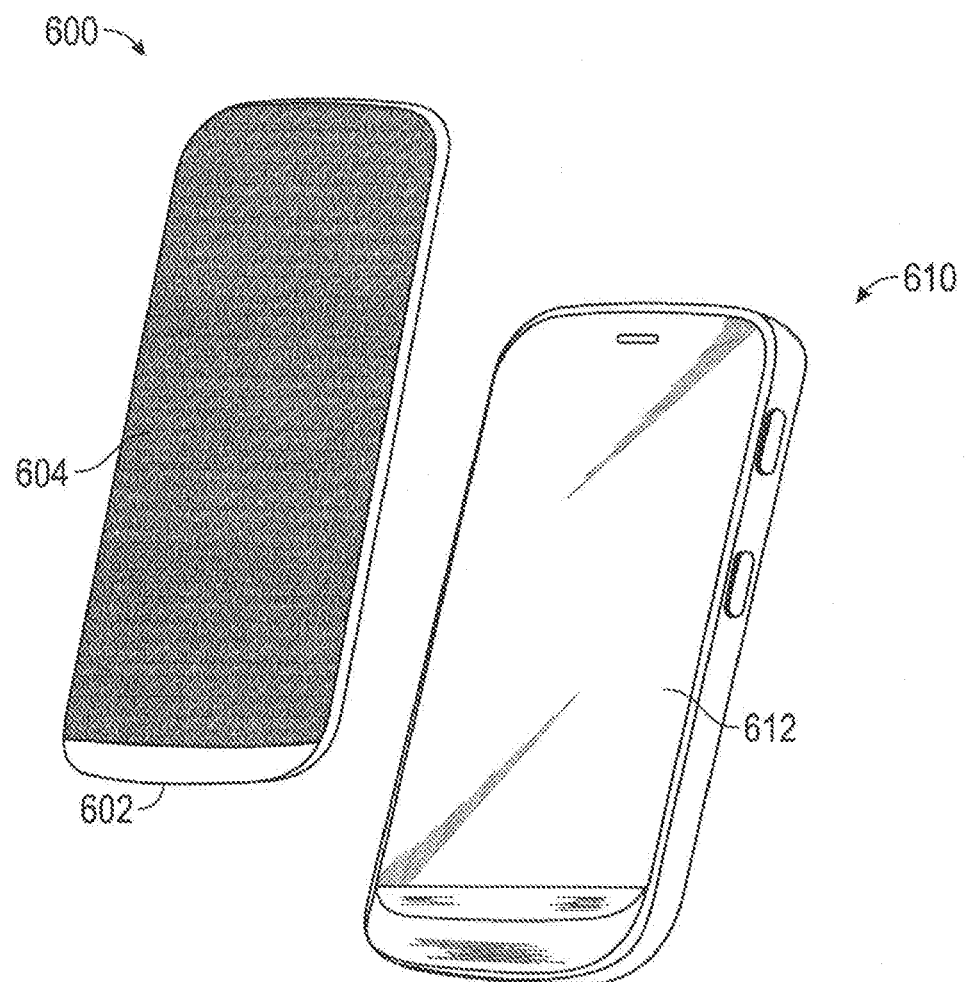
FIG. 6 is an environmental view of a system according to an embodiment of the invention.

Referring now to FIG. 6, an embodiment of the invention is depicted. In the present embodiment, a filtering system 600 is provided. The filtering system 600 may be configured to selectively filter light passing therethrough to. More specifically, the filtering system 600 may be configured to filter light to reduce or eliminate light within one or more wavelength ranges so as to affect or prevent a biological response in an observer. Furthermore, the filtering system 600 may be configured to filter light so as to affect a shift in the circadian rhythm of an observer. In some embodiments, the filtering system 600 may be configured to be attached to a display, such as the display 440 of FIGS. 4*a-b*. Accordingly, the filtering system 600 presents an alternative to controlling the operation of the light source 420 of the user device 400 so as to affect a shift to the circadian rhythm of the observer.

In the present embodiment, the filtering system 600 comprises a frame 602. The frame 602 may be configured to be positioned adjacent or attached to a device configured to emit light. In the present embodiment, the frame 602 is configured to attach to a user device 610 having a display 612. The user device 610 and its constituent elements are not part of the embodiment of the invention. Instead, only the filtering system 600 is part of the present embodiment. The filtering system 600 may further comprise a filter 604. The filter 604 may be carried by the frame 602. Moreover, the frame 600 may be configured so as to position the filter 604 adjacent to the display 612 such that light emitted from the display must pass through the filter 604 prior to being observable by an observer. Accordingly, the filter 604 may be configured to as to permit all light emitted by the display 612 to pass therethrough into the environment. Moreover, the filter 604 may be configured to reduce the intensity of or substantially eliminate light within a wavelength range. The wavelength range associated with the filter 604 may be any wavelength range that is associated with a biological effect in an observer. In the present embodiment, the filter 604 may be configured to substantially reduce or eliminate the intensity of lighting within a wavelength range from about 420 nm to about 490 nm. All other ranges of wavelengths are contemplated and included within the scope of the invention.

In the present embodiment, the user device 610 is a mobile phone, specifically, a smart phone. Any type of device that generates light is contemplated and included within the scope of the invention, including other computerized devices, such as personal computers, as well as devices intended for providing illumination, such as light bulbs, lamps, lanterns, light fixtures, and the like.

The filter 604 may be any filtering device or material as is known in the art. In some embodiments, the filter 604 may be configured to persistently and continuously filter all light passing therethrough, such as a notch filter. In some embodiments, the filter 604 may be configured to be operable to, in a first setting, filter light passing therethrough, and in a second setting, to allow light to pass therethrough unfiltered, hereinafter referred to as an active filter. Such filters are known in the art, utilizing metamaterials known to be selectively operable to filter electromagnetic radiation in the visible spectrum frequency range. In such embodiments, the filtering system 600 may further comprise control circuitry positioned in electrical communication with the filter 604, as well as a power storage device, each as described hereinabove, except to the extent that the control circuitry is configured to control the transition of the filter 604 between the first and second settings, as described. More specifically, the control circuitry may be configured to adjust the filter 604 responsive to a preconditioning schedule so as to affect a circadian shift in an observer as described hereinabove.

Figure 7:
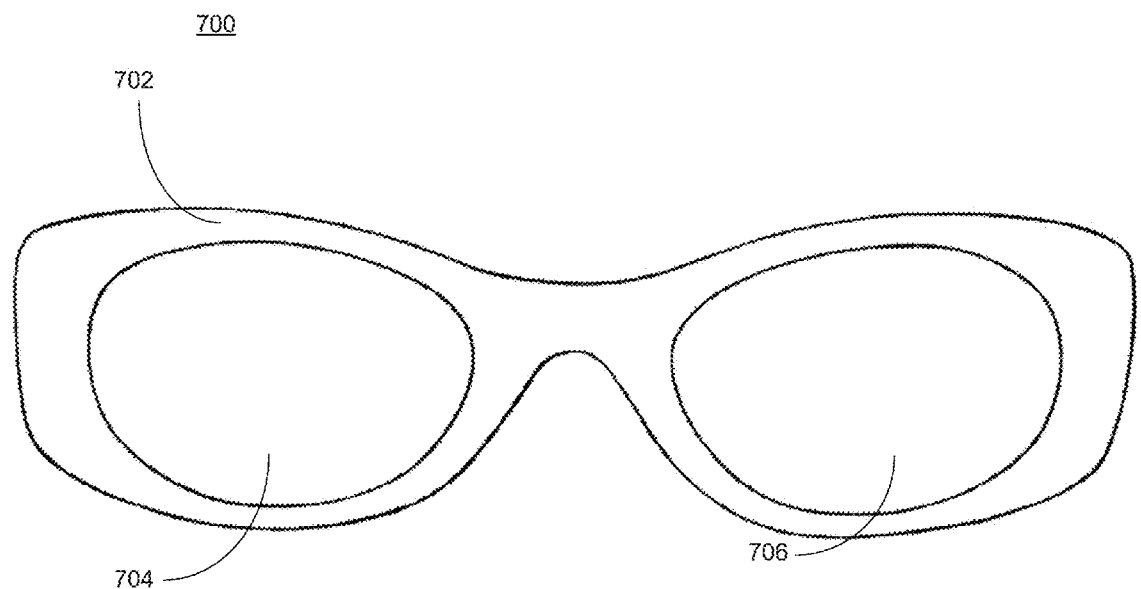
FIG. 7 is an environmental view of a system according to an embodiment of the invention.

Referring now to FIG. 7, an embodiment of the invention is presented. As in the embodiment depicted in FIG. 6, the embodiment comprises a filtering system 700 configured to substantially reduce or eliminate light within a wavelength range from light passing therethrough. However, the filtering system 700 comprises a frame 702 configured to be carried by the ears and nose of an observer, such that the filtering system functions as sun glasses, as is known in the art. Accordingly, the filtering system may be configured to filter light passing therethrough, either from one or more artificial light sources, such as luminaires or light fixtures, or from a natural light source, such as the sun, and from combinations thereof. Moreover, the filtering system may comprise a first filter 704 and a second filter 706, one for each eye of an observer. The first and second filters 704, 706 may include any of the features described for the filter 604 as described hereinabove.

Figure 8:
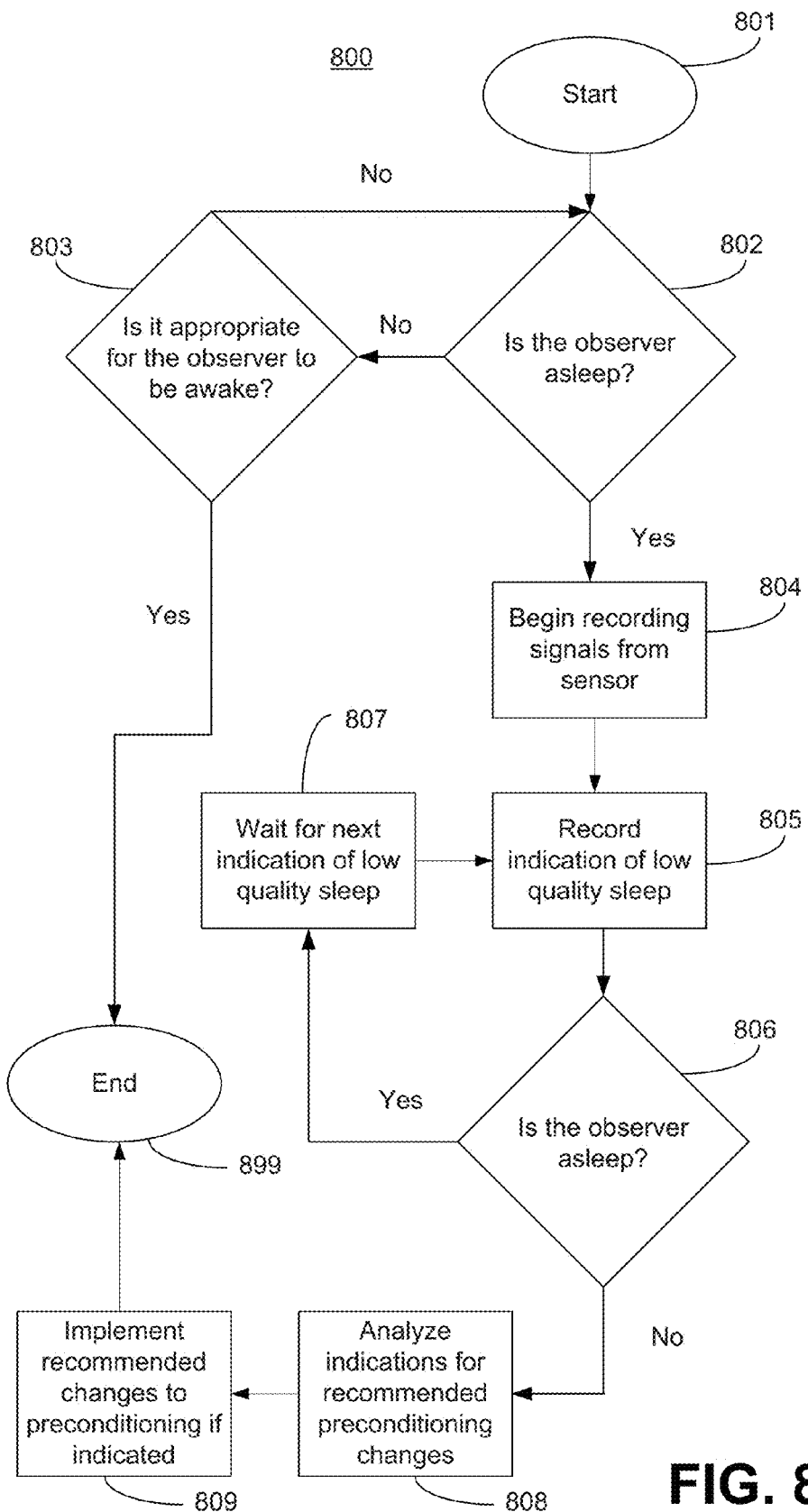
FIG. 8 is a method of monitoring and evaluating the quality of sleep and adjusting a preconditioning schedule responsive thereto according to an embodiment of the invention.

Referring now to FIG. 8, a method according to an embodiment of the invention is presented. FIG. 8 discloses a flow chart illustrating a method 800 of monitoring the quality of sleep of an observer, and altering a preconditioning schedule responsive thereto. The system may include a controller and a sensor for monitoring an indication of the quality of sleep. In some embodiments, the system may be the same system configured to perform the steps illustrated in FIGS. 1-3. In some embodiments, the system may be discrete from the system described in FIGS. 1-3 and may further comprise a communication device configured to communicate with the system described in FIGS. 1-3, either directly or across a network.

Starting at Block 801, the system may determine if the observer is asleep at Block 802. Such a determination may be inferred based on the type of indication received from the sensor. The sensor may be any type of device that may generate a signal receivable by the system from which the quality of sleep of the observer may be inferred. Types of sensors include, but are not limited to, motion detectors, including optically-based detectors, such as LEDs and reverse-biased LEDs, and wearable systems, such as accelerometer-based systems, occupancy sensors, and the like. In some systems, such as accelerometer-based sensor systems, the sensor may be worn by the observer. Moreover, the sensor may be positioned in electrical communication with the controller by any means or method known in the art, including wired and wireless communication, as described hereinabove. More information regarding the monitoring of an observer may be found in U.S. patent application Ser. No. 13/564,345 titled Occupancy Sensor and Associated Methods filed May 4, 2012, U.S. patent application Ser. No.

13/269,222 titled Wavelength Sensing Light Emitting Semiconductor and Associated Methods filed Oct. 7, 2011, and U.S. patent application Ser. No. 13/739,665 titled Motion Detection System and Associated Methods filed Jan. 11, 2013, the contents of which are incorporated by reference herein in their entirety, except to the extent disclosure therein is inconsistent with disclosure herein, and U.S. Provisional Patent Application Ser. No. 61/936,654 which is incorporated by reference hereinabove.

If the observer is determined not to be asleep at Block 802, then at Block 803 the system may determine if the time of day indicates it is appropriate for the observer to be awake at Block 803. Such a determination may be based on a default sleeping time, i.e. about 10 PM to about 6 AM, or it may be based on a learned schedule of the observer, as discussed hereinabove. If it is determined that it is appropriate for the observer to be awake, the method 800 may end at Block 899. If it is determined it is not appropriate for the observer to be awake, the method 800 may return to Block 802. In some embodiments, the system may provide an alert to the observer indicating that it is time to sleep according to any method of alert described herein.

If, at Block 802, it is determined the observer is asleep, the system may begin recording signals from the sensor at Block 804. The signals from the sensor may indicate the quality of sleep of the observer. In that case of motion sensors, an indication of motion may be understood to mean lower quality sleep. Each indication of low quality sleep may be recorded by the system.

At Block 805, a signal indicating low quality sleep is received by the system. At Block 806, the system may determine whether the observer is still asleep, similar to the determination made at Block 802. If it is determined the observer is still asleep, then the system may record the signal indicating low quality sleep at Block 806. Upon recoding the signal, the method 800 may proceed to Block 807, wherein the system waits for the next signal indicating low quality sleep. Upon such a signal, the method 800 may return to Block 805.

If, at Block 806 it is determined the observer is no longer asleep, the system may analyze the recorded indications of low quality asleep to determine if a change to the preconditioning schedule is recommended at Block 808. The determination may be made based upon a number of indications received from the sensor. If the number of indications is equal to or exceeds a threshold number, then the system may recommend changing the preconditioning schedule. Such a change may take the form of reducing the shift scheduled to occur in the day following the previous sleeping cycle. Any other types of changes, including increasing the shift, as well as suggesting various activities to the observer to promote higher quality sleep, is contemplated and included within the scope of the invention. At Block 809, any recommended changes to the preconditioning schedule, if indicated, may be implemented, and the method 800 may end at Block 899.

Figure 9:
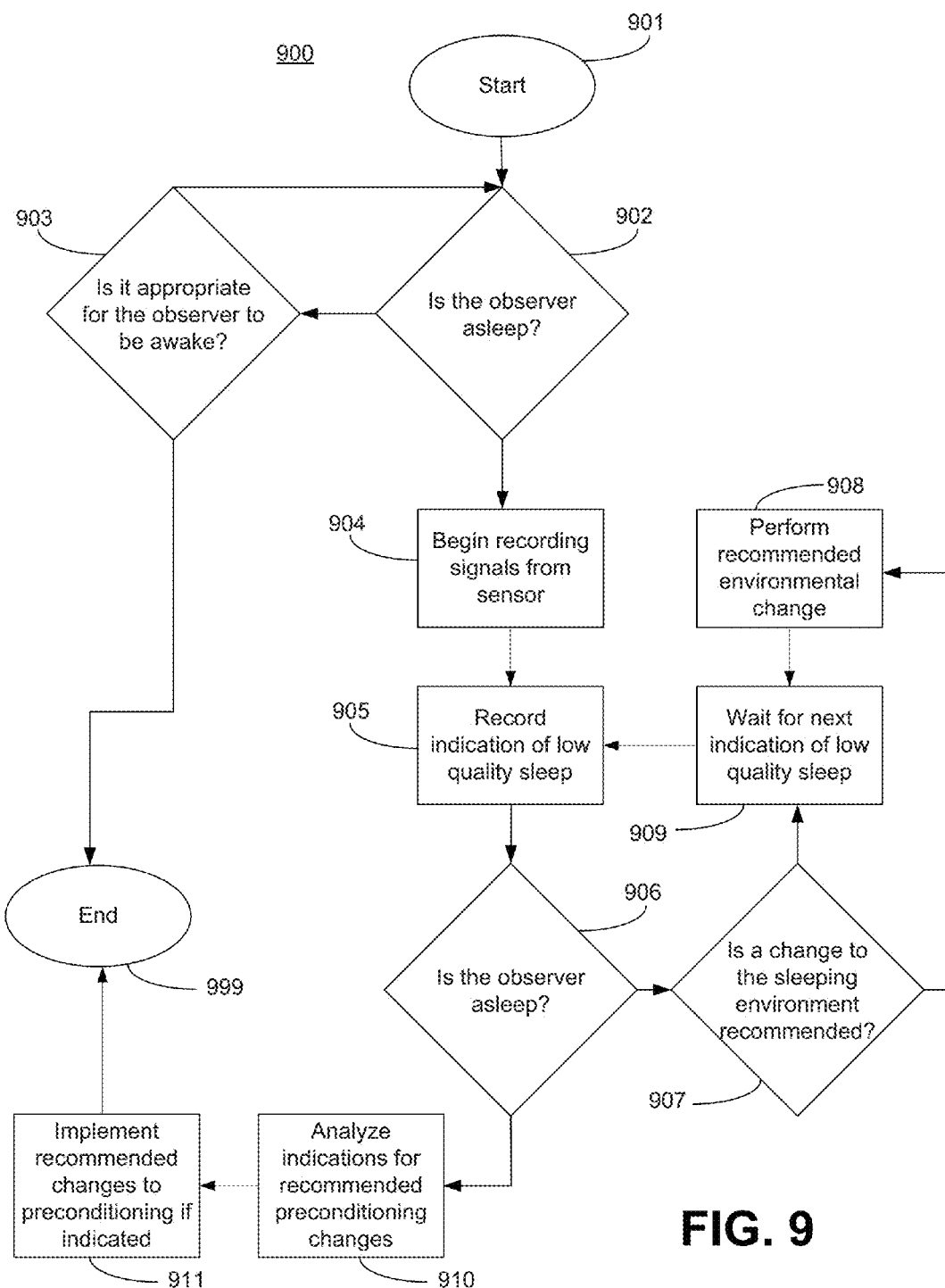
FIG. 9 is a method for monitoring the quality of sleep of an individual and adjusting various environmental factors responsive thereto according to an embodiment of the invention

Referring now to FIG. 9, a flow chart illustrating a method 900 for monitoring and improving the quality of sleep of an observer is presented. The method may be performed by a system for monitoring the quality of sleep and altering the environment within which the observer is sleeping responsive to indications of low quality sleep to improve the quality of sleep thereof. The system may be substantially similar to that of the system performing the method 800 of FIG. 8, further including one or more environmental control devices positioned in electrical communication with and being operable by the controller. Types of environmental control devices include, but are not limited to, HVAC systems, ceiling fans, floor fans, and noise generating devices.

Similar to method 800 of FIG. 8, method 900 may begin at Block 901, and then may determine if the observer is asleep at Block 902. If the observer is determined not to be asleep at Block 902, then at Block 903 the system may determine if the time of day indicates it is appropriate for the observer to be awake, as discussed hereinabove. If it is determined that it is appropriate for the observer to be awake, the method 900 may end at Block 999. If it is determined it is not appropriate for the observer to be awake, the method 900 may return to Block 902.

If, at Block 902, it is determined the observer is asleep, the system may begin recording signals from the sensor at Block 904. The signals from the sensor may indicate the quality of sleep of the observer. In that case of motion sensors, an indication of motion may be understood to mean lower quality sleep. Each indication of low quality sleep may be recorded by the system.

At Block 905, a signal indicating low quality sleep is received by the system. At Block 906, the system may determine whether the observer is still asleep, similar to the determination made at Block 902. Upon recoding the signal, the method 900 may proceed to Block 907, wherein the system determines whether a change to the sleeping environment is recommended responsive to the indication of low quality sleep received at Block 905. Such a determination may be made based on a number of factors, including the number of indications received within a timeframe, such as the previous five minutes. Such a timeframe is exemplary only, and any timeframe is contemplated and included within the scope of the invention.

Additionally, the determination may be made based on the potential for adverse sleeping conditions to be present, and the ability of the environmental control device to address such conditions. For example, where the environmental control device is an HVAC system, such systems typically include a thermometer that measures the temperature of air within a space and provides an indication thereof. Where the temperature is indicated to be outside a target temperature range for sleeping, the system may operate the HVAC system so as to bring the temperature to within the range. Where the environmental control system is a fan, the system may operate the fan, either increasing or decreasing the flow generated thereby, to accordingly alter the perceived temperature by the observer such that the perceived temperature falls within the target temperature range. In some embodiments, the environmental control system is a noise generating device, the system may alternatively increase or decrease the noise generated thereby, or, when possible, alter the type of noise generated, so as to encourage sleep in the observer. Such examples of environmental control devices are exemplary only, and any other type of environmental control device, as well as methods of operation, are contemplated and included within the scope of the invention.

If the determination is made at Block 907 to change the sleeping environment, the system may operate the environmental control device as described hereinabove at Block 908. Then, at Block 909, the system may wait for the next signal indicating low quality sleep. When such a signal is received, the method 900 may return to Block 905.

If the determination is made at Block 907 not to change the sleeping environment, the method 900 may proceed to Block 909.

If, at Block 906, it is determine the observer is no longer asleep, the system may analyze the recorded indications of low quality asleep to determine if a change to the preconditioning schedule is recommended at Block 910, as described. hereinabove for FIG. 8. Additionally, any changes to the preconditioning schedule may be performed at Block 911, and the method 900 may end at Block 999.

Some of the illustrative aspects of the present invention may be advantageous in solving the problems herein described and other problems not discussed which are discoverable by a skilled artisan.

While the above description contains much specificity, these should not be construed as limitations on the scope of any embodiment, but as exemplifications of the presented embodiments thereof. Many other ramifications and variations are possible within the teachings of the various embodiments. While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. A method of dynamically adjusting a circadian rhythm comprising the steps of:
   determining a current circadian rhythm status of a circadian rhythm of an observer;
   accessing a calendar of the observer;
   identifying one or more future events of the observer to precondition for, defined as identified future events;
   determining a preconditioning schedule for each of the identified future events, comprising the steps of:
      identifying the type of circadian shift needed for the future event;
      determining if the any of the preconditioning schedules for the multiple identified future events conflict;
      upon a determination that a conflict exists, performing the steps of:
         querying a user to select one or more non-conflicting future events,
         receiving an input from the user indicating one or more future events to precondition for, and
         modifying the preconditioning schedules responsive to the input;
      determining the magnitude of the circadian shift;
      determining the timeframe for preconditioning;
      determining the magnitude of the per-day shift; and
      determining if the per-day shift exceeds a maximum allowed per-day shift;
      upon a determination that the per-day shift exceeds the maximum allowed per-day shift, performing the steps of:
         querying the user as to whether to override the maximum allowed per-day shift,
         receiving an input from the user responsive to the query of whether to exceed the maximum per-day shift, and
         selecting a preconditioning schedule responsive to the user input;
   establishing communication with a light source; and
   operating the light source to emit light of the preconditioning schedule.

2. The method of claim 1 further comprising the steps of:
   determining the time zone within which the future event will occur;
   determining the time of day for the observer; and
   determining the date.

3. The method of claim 1 wherein the maximum allowed per-day shift is 2.5 hours.

4. The method of claim 1 further comprising the steps of:
   monitoring a sleep cycle of the observer; and
   implementing changes to the preconditioning schedule responsive to the sleep cycle of the observer.

5. The method of claim 4 wherein the step of monitoring a sleep pattern of the observer comprises the steps of:
   determining if the observer is asleep;
   recording signals from a sensor;
   identifying and recording an indication of low quality sleep from the signals received from the sensor; and
   determining changes to the preconditioning schedule responsive to the indication of the low quality sleep.

6. The method of claim 5 wherein the sensor is at least one of an optical motion detector and an acceleration detector.

7. The method of claim 5 further comprising the step of iteratively observing if the observer is asleep, recording indications of low quality sleep, and waiting for the next indication of low quality sleep until the observer is awake.

8. The method of claim 5 wherein responsive to an indication of low quality sleep, performing the steps of:
   determining whether an environmental condition of a sleeping environment associated with the observer is outside a target range, defined as an environmental change recommendation; and
   signaling an environmental control system responsive to the environmental change recommendation.

9. The method of claim 8 wherein the environmental control system is an HVAC system.

10. A method of dynamically adjusting a circadian rhythm comprising the steps of:
   determining a current circadian rhythm status of a circadian rhythm of an observer;
   determining the time of day for the observer;
   determining the time zone of the observer;
   determining the date;
   accessing a calendar of the observer;
   identifying one or more future events of the observer to precondition for, defined as identified future events;
   determining a preconditioning schedule responsive to the identified future events, comprising the steps of:
      identifying the type of circadian shift needed for the future event;
      determining if the any of the preconditioning schedules for the multiple identified future events conflict,
      upon a determination that a conflict exists, performing the steps of:

querying a user to select one or more non-conflicting future events,
receiving an input from the user indicating one or more future events to precondition for, and
modifying the preconditioning schedules responsive to the input, and
upon a determination that no conflict exists, performing the steps of:
determining the magnitude of the circadian shift, including determining the difference in time zones between the time zone of the observer and the time zone within which the future event will occur,
determining the timeframe for preconditioning,
determining the magnitude of the per-day shift,
determining if the per-day shift exceeds a maximum allowed per-day shift,
upon a determination that the per-day shift exceeds the maximum allowed per-day shift, performing the steps of:
querying the user as to whether to override the maximum allowed per-day shift,
receiving an input from the user responsive to the query of whether to exceed the maximum per-day shift, and
selecting a preconditioning schedule responsive to the user input; and
establishing communication with a light source; and
operating the light source to emit light of the preconditioning schedule.

11. The method of claim 10 further comprising the steps of:
determining if the observer is asleep;
recording signals from a sensor;
identifying and recording an indication of low quality sleep from the signals received from the sensor; and
determining changes to the preconditioning schedule responsive to the indication of the low quality sleep.

12. The method of claim 11 further comprising the step of iteratively observing if the observer is asleep, recording indications of low quality sleep, and waiting for the next indication of low quality sleep until the observer is awake.

13. The method of claim 11 wherein responsive to an indication of low quality sleep, performing the steps of:
determining whether an environmental condition of a sleeping environment associated with the observer is outside a target range, defined as an environmental change recommendation; and
signaling an environmental control system responsive to the environmental change recommendation.

14. A lighting system for dynamically adjusting a circadian rhythm of an observer comprising:
a lighting device comprising:
a housing
a control circuitry,
a memory, and
a light source positioned in communication with and controlled by the control circuitry;
wherein the memory comprises a calendar associated with the user comprising a future event;
wherein the control circuitry is configured to identify one or more future events from the calendar to precondition a circadian rhythm of the observer, defined as the identified future events;
wherein the control circuitry is configured to determine a preconditioning schedule for the identified future events comprising the steps of:
identifying the type of circadian shift needed for the future event;
determining if the any of the preconditioning schedules for the multiple identified future events conflict;
upon a determination that a conflict exists, performing the steps of:
querying a user to select one or more non-conflicting future events,
receiving an input from the user indicating one or more future events to precondition for, and
modifying the preconditioning schedules responsive to the input;
determining the magnitude of the circadian shift;
determining the timeframe for preconditioning; and
determining the magnitude of the per-day shift;
determining if the per-day shift exceeds a maximum allowed per-day shift;
upon a determination that the per-day shift exceeds the maximum allowed per-day shift, performing the steps of:
querying the user as to whether to override the maximum allowed per-day shift,
receiving an input from the user responsive to the query of whether to exceed the maximum per-day shift, and
selecting a preconditioning schedule responsive to the user input; and
wherein the control circuitry is configured to operate the light source according to the preconditioning schedules.

15. The lighting system of claim 14 wherein the lighting device further comprises a communication device positioned in communication with the control circuitry and configured to communicate across a network; and wherein the communication device is configured to access a calendar and identify future events associated with the observer across the network.

* * * * *